(12) United States Patent
Han

(10) Patent No.: US 10,306,887 B2
(45) Date of Patent: Jun. 4, 2019

(54) COMPOSITION AND METHODS FOR MODULATION OF THE OCTOPAMINE RECEPTOR AND ITS HOMOLOGS

(71) Applicant: Kyung-an Han, El Paso, TX (US)

(72) Inventor: Kyung-an Han, El Paso, TX (US)

(73) Assignee: THE BOARD OF REGENTS OF THE UNIVERSITY OF TEXAS SYSTEMS, Austin, TX (US)

( * ) Notice: Subject to any disclaimer, the term of this patent is extended or adjusted under 35 U.S.C. 154(b) by 0 days.

(21) Appl. No.: 15/501,504

(22) PCT Filed: Aug. 4, 2015

(86) PCT No.: PCT/US2015/043536
§ 371 (c)(1),
(2) Date: Feb. 3, 2017

(87) PCT Pub. No.: WO2016/022520
PCT Pub. Date: Feb. 11, 2016

(65) Prior Publication Data
US 2017/0223962 A1     Aug. 10, 2017

Related U.S. Application Data

(60) Provisional application No. 62/033,628, filed on Aug. 5, 2014.

(51) Int. Cl.
| | |
|---|---|
| *A01N 47/22* | (2006.01) |
| *C07K 14/435* | (2006.01) |
| *A01N 33/04* | (2006.01) |
| *A01N 33/06* | (2006.01) |
| *A01N 43/50* | (2006.01) |
| *A01N 45/02* | (2006.01) |
| *C12Q 1/6897* | (2018.01) |
| *G01N 33/50* | (2006.01) |

(52) U.S. Cl.
CPC .............. *A01N 47/22* (2013.01); *A01N 33/04* (2013.01); *A01N 33/06* (2013.01); *A01N 43/50* (2013.01); *A01N 45/02* (2013.01); *C07K 14/43563* (2013.01); *C12Q 1/6897* (2013.01); *G01N 33/5041* (2013.01); *G01N 2333/43552* (2013.01)

(58) Field of Classification Search
CPC ....................................................... A01N 47/22
See application file for complete search history.

(56) References Cited

U.S. PATENT DOCUMENTS

| | | | |
|---|---|---|---|
| 5,202,242 A | 4/1993 | Mynderse et al. | ............... 435/76 |
| 5,362,634 A | 11/1994 | Boeck et al. | ................... 435/76 |
| 5,496,931 A | 3/1996 | Boeck et al. | ................... 536/7.1 |
| 5,571,901 A | 11/1996 | Boeck et al. | ................... 536/7.1 |
| 5,591,606 A | 1/1997 | Turner et al. | ................... 435/76 |
| 5,631,155 A | 5/1997 | Turner et al. | ............... 435/252.1 |
| 5,670,364 A | 9/1997 | Mynderse et al. | ......... 435/252.1 |
| 5,670,486 A | 9/1997 | Mynderse et al. | ............... 514/28 |
| 5,767,253 A | 6/1998 | Turner et al. | ................... 536/6.5 |
| 5,840,861 A | 11/1998 | Mynderse et al. | ........... 536/16.8 |
| 6,001,981 A | 12/1999 | DeAmicis et al. | ............ 536/7.1 |
| 6,800,614 B2 | 10/2004 | Lewer et al. | ................... 514/28 |
| 6,919,464 B1 | 7/2005 | Crouse et al. | ................. 549/266 |
| 2014/0045696 A1 | 2/2014 | Bretschneider et al. | ..... 504/283 |

FOREIGN PATENT DOCUMENTS

| | | | |
|---|---|---|---|
| WO | WO/85/005038 | 11/1985 | |
| WO | WO/99/21891 | 5/1999 | |
| WO | WO/00/026634 | 5/2000 | |
| WO | WO/00/050630 | 8/2000 | |
| WO | WO/10/052276 | 5/2010 | |
| WO | WO2010/052276 | * 5/2010 | ............. G01N 33/68 |

OTHER PUBLICATIONS

Agnew et al. "The gastrointestinal peptide obestatin induces vascular relaxation via specific activation of endothelium-dependent NO signaling " *Br. J. Pharmacol.* 2012, 166:327-338.
Aigaki et al. "Ectopic expression of sex peptide alters reproductive behavior of female D. melanogaster." *Neuron.* 1991, 7(4) :557-563.
Akbari et al. *BMC Cell Biol.* 2009, 10:8.
Anonymous, "Apis melliflera octopamine receotir beta-2R(Octbeta2R), transcript variant X7, mRNA" GenBank, Jan. 7, 2014, pp. 1-3 http://www.ncbi.nlm.nih.gov/nuccore/5715, retrieved on Oct. 13, 2015.
Balfanz et al. "A family of octopamine [corrected] receptors that specifically induce cyclic AMP production or Ca2+ release in *Drosophila melanogaster.*" *J. Neurochem.* 2005, 93(2):440-451.
Booth. "Effects of biogenic amines and adrenergic drugs on oviposition in the cattle tick Boophilus: evidence for octopaminergic innervation of the oviduct." *Exp. Appl. Acarol.* 1989, 7(4):259-266.
Chen et al. *Genetics.* 2013, 193:159-176.
Chen et al. "Functional and pharmacological characterization of a beta-adrenergic-like octopamine receptor from the silkworm *Bombyx mori.*" *Insect Biochem. Mol. Biol.* 2010, 40(6):476-486.
Cole, et al., J Biolog Chem. 280(15):14948-55, 2005.

(Continued)

*Primary Examiner* — Paul V Ward
(74) *Attorney, Agent, or Firm* — Norton Rose Fulbright US LLP

(57) ABSTRACT

Embodiments of the invention are directed of compositions for activation or inhibition of the Octβ2 receptor and uses thereof. The inventors have discovered that the beta adrenergic-like octopamine receptor Octβ2 serves as a key signaling molecule for ovulation and recruits protein kinase A and Ca2+/calmodulin-sensitive kinase II as downstream effectors for this activity. Octβ2R homozygous mutant females are sterile, and display normal courtship, copulation, sperm storage and post-mating rejection behavior but were unable to lay eggs.

7 Claims, 11 Drawing Sheets

Specification includes a Sequence Listing.

(56) References Cited

OTHER PUBLICATIONS

Cossio-Bayugar et al. "Perturbation of tyraminergic/octopaminergic function inhibits oviposition in the cattle tick *Rhipicephalus* (*Boophilus*) *microplus*." *J. Insect Physiol.* 2012, 58(5):628-633.
Crocker et al. *Neuron.* 2010, 65:670-681.
Daborn et al. "A single p450 allele associated with insecticide resistance in *Drosophila.*" *Science.* 2002, 297(5590):2253-2256.
Drazen et al. "Reproductive function in female mice lacking the gene for endothelial nitric oxide synthase " *Nitric Oxide.* 1999, 3(5):366-374.
Evans et al.. "Insect octopamine receptors: a new classification scheme based on studies of cloned *Drosophila* G-protein coupled receptors." *Invert. Neurosci.* 2005, 5(3):111-118.
Farooqui et al. *J. Neurosci.* 2003, 23:5370-5380.
Flybase Consortium. *Nucleic Acids Res.* 2003, 31:172-175.
Gabler et al. *Genetics.* 2005, 169:723-736.
Han et al. *J. Neurosci.* 1998, 18:3650-3658.
Hasemeyer et al. *Neuron.* 2009, 61:511-518.
Helm et al. "Quantitative pharmacological characterization of beta-receptors and two types of alpha-receptors mediating sympathomimetic smooth muscle response in the human Fallopian tube at various cyclic stages." *Acta Physiol. Scand.* 1982, 114(3):425-432.
International Search Report and Written Opinion in International Application No. PCT/US2015/043536 dated Nov. 6, 2015.
Isaac et al. *Proc. Biol. Sci.* 2010, 277:65-70.
Jones et al. *Am. J. Physiol. Heart Circ. Physiol.* 2007, 292:H2634-2642.
Kapelnikov et al. *BMC Dev. Biol.* 2008, 8:114.
Khan et al. "Evidence for the presence of beta-3-adrenoceptors mediating relaxation in the human oviduct." *Pharmacology.* 2005, 74(3):157-162.
Kiger et al. *Genetics.* 1999, 152:281-290.
Kim et al. *Genes Brain Behav.* 2007, 6:201-207.
Kim et al. *J. Neurosci.* 2013, 33:1672-1677.
Lee et al. *PLoS One.* 2009, 4:e4716.
Lee, et al., Dev Biol. 264:179-90, 2003.
Li et al., Archives Insect Biochem Physiol. 88(3):168-78, 2014.
Lim, et al., PLoS One, 9(8):1-13, 2014.
Maqueira, et al., J Neurochem. 94(2):547-60, 2005.
Middleton et al. *BMC Biol.* 2006, 4:17.
Monastirioti et al. *J. Comp. Neurol.* 1995, 356:275-287.
Monastirioti et al. *J. Neurosci.* 1996, 16:3900-3911.
Monastirioti. "Distinct octopamine cell population residing in the CNS abdominal ganglion controls ovulation in *Drosophila melanogaster.*" *Dev. Biol.* 2003, 264(1):38-49.
Nykamp et al. "Interaction between octopamine and proctolin on the oviducts of Locusta migratoria." *J. Insect Physicol.* 2000, 46(5):809-816.
Peng et al. *Current Biology.* 2005, 15:1690-1694.
Rezaval et al. *Current Biology.* 2012, 22:1155-1165.
Ribeiro et al. *Current Biology.* 2010, 20:1000-1005.
Rodriguez-Valentin et al. "Oviduct contraction in *Drosophila* is modulated by a neural network that is both, octopaminergic and glutamatergic." *J. Cell. Physiol.* 2006, 209(1):183-198.
Roeder. "Tyramine and octopamine: ruling behavior and metabolism." *Annu. Rev. Entomol.* 2005, 50(1):447-477.
Schmidt, et al., Insect Biochem Molec Biol. 23(5):571-9, 1993.
Schneider et al. *Am. J. Physiol. Heart Circ. Physiol.* 2003, 284:H2311-2319.
Schwaerzel et al. *J. Neurosci.* 2003, 23:10495-10502.
Sinakevitch et al. "Comparison of octopamine-like immunoreactivity in the brains of the fruit fly and blow fly." *J. Comp. Neurol.* 2006, 494(3):460-475.
Tay et al. "Human tubal fluid: production, nutrient composition and response to adrenergic agents." *Hum. Reprod.* 1997, 12(11):2451-2456.
Unoki et al. "Participation of octopaminergic reward system and dopaminergic punishment system in insect olfactory learning revealed by pharmacological study." *Eur. J. Neurosci.* 2005, 22(6):1409-1416.
Wu et al. *J. Exp. Biol.* 2012, 215:2646-2652.
Yamane et al. "Reduced female mating receptivity and activation of oviposition in two *Callosobruchus* species due to injection of biogenic amines." *J. Insect Physiol.* 2010, 56(3):271-276.
Yang et al. *Neuron.* 2009, 61:519-526.
Yapici et al. "A receptor that mediates the post-mating switch in *Drosophila* reproductive behaviour." *Nature.* 2008, 451(7174):33-37.
Zhou et al. *The Journal of neuroscience: the official journal of the Society for Neuroscience.* 2012, 32:14281-14287.

* cited by examiner

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
```
tgtgcagcca ctggactatc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
tatggcgtat gccttgttca                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
agcatcatgc acctctgttg                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gtgtaccatc ccgagcagat                                              20

<210> SEQ ID NO 5
<211> LENGTH: 19
<212> TYPE: DNA
<213> ORGANISM: Artificial Sequence
<220> FEATURE:
<223> OTHER INFORMATION: Synthetic Primer

<400> SEQUENCE: 5
atttcagtgc agcgcaatc                                               19

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
catccaggct gttgtacacg                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ttccacgttt gagctcctct                                              20

<210> SEQ ID NO 8
<211> LENGTH: 20
<212> TYPE: DNA
<213> ORGANISM: Artificial Sequence

```
<220> FEATURE:
<223> OTHER INFORMATION: Synthetic Primer

<400> SEQUENCE: 8
gccagcgaca caacaaagta                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
tacaggccca agatcgtgaa                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
gttcgatccg taaccgatgt                                               20

<210> SEQ ID NO 11
<211> LENGTH: 19
<212> TYPE: DNA
<213> ORGANISM: Artificial Sequence
<220> FEATURE:
<223> OTHER INFORMATION: Synthetic Primer

<400> SEQUENCE: 11
cgcaccaagc acttcatcc                                                19

<210> SEQ ID NO 12
<211> LENGTH: 18
<212> TYPE: DNA
<213> ORGANISM: Artificial Sequence
<220> FEATURE:
<223> OTHER INFORMATION: Synthetic Primer

<400> SEQUENCE: 12
agcggcgacg cactctgt                                                 18
```

COMPOSITION AND METHODS FOR MODULATION OF THE OCTOPAMINE RECEPTOR AND ITS HOMOLOGS

This Application is a national phase application under 35 U.S.C. § 371 of International Application No. PCT/US2015/043536, filed Aug. 4, 2015, which claims priority to U.S. Provisional Patent Application 62/033,628 filed Aug. 5, 2014. Both applications are hereby incorporated by reference in their entirety.

STATEMENT REGARDING FEDERALLY FUNDED RESEARCH

This invention was made with government support under 2010-65105-20625 awarded by the United States Department of Agriculture, and MD007592 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Mating triggers comprehensive physiological and behavioral changes in female insects to maximize reproductive success. Notably, sex peptide, a seminal fluid protein transferred during copulation, activates oviposition, enhances locomotor activity, decreases sexual receptivity, shortens daytime sleep, and alters immunity and food choice in *Drosophila melanogaster* (Aigaki et al. *Neuron*. 1991, 7:557-563; Isaac et al. *Proc. Biol. Sci.* 2010, 277:65-70; Peng et al. *Current Biology*. 2005, 15:1690-1694; Ribeiro and Dickson. *Current Biology*. 2010, 20:1000-1005). While broadly present in the reproductive, endocrine and nervous systems, the sex peptide receptor expressed in the fruitless, pickpocket, and doublesex neurons in particular plays a central role in reducing sexual receptivity and increasing oviposition processes that directly and substantially contribute to fecundity (Yapici et al. *Nature*. 2008, 451:33-37; Yang et al. *Neuron*. 2009, 61:519-526; Hasemeyer et al. *Neuron*. 2009, 61:511-518; Rezaval et al. *Current Biology*. 2012, 22:1155-1165). Information regarding the downstream effectors and signaling pathways, however, is largely unknown. Enhanced understanding of the molecules and target sites mediating individual post-mating processes is needed to narrow the knowledge gap and gain insights into an effective strategy to control female fecundity.

Oviposition is induced upon mating in most insects. Ovulation is a primary step in oviposition, representing an important target to control insect pests and vectors, but limited information is available on the underlying mechanism.

There is a need for additional compositions and methods for the control of pest and insect populations.

SUMMARY

The inventors have discovered that the beta adrenergic-like octopamine receptor Octβ2R serves as a key signaling molecule for ovulation and recruits protein kinase A and Ca2+/calmodulin-sensitive kinase II as downstream effectors for this activity. Octβ2r homozygous mutant females are sterile, and display normal courtship, copulation, sperm storage and post-mating rejection behavior but were unable to lay eggs. It was previously shown that octopamine neurons in the abdominal ganglion innervate the oviduct epithelium. Consistently, restored expression of Octβ2R in oviduct epithelial cells was sufficient to reinstate ovulation and full fecundity in the octβ2r mutant females, demonstrating that the oviduct epithelium is a major site of Octβ2R's function in oviposition. It was also found that overexpression of the protein kinase A catalytic subunit or Ca2+/calmodulin-sensitive protein kinase II led to partial rescue of octβ2r's sterility. This suggests that Octβ2R activates cAMP as well as additional effectors including Ca2+/calmodulin-sensitive protein kinase II for oviposition. All three known beta adrenergic-like octopamine receptors stimulate cAMP production in vitro. Octβ1R, when ectopically expressed in the octβ2r's oviduct epithelium, fully reinstated ovulation and fecundity. Ectopically expressed Octβ3R, on the other hand, partly restored ovulation and fecundity while OAMB-K3 and OAMB-AS that increase Ca2+ levels yielded partial rescue of ovulation but not fecundity deficit. These observations suggest that Octβ2R have distinct signaling capacities in vivo and activate multiple signaling pathways to induce egg laying.

Embodiments are directed to the use of certain octopamine analogs and derivatives thereof as ligands for the Octβ2R and its mammalian homologs. Certain aspects are directed to the use of octopamine analogs as a means of screening for agonists and antagonists of Octβ2R and ovulation. More specifically, the present invention discloses that particular derivatives of octopamine that are modified so that they selectively activate or antagonize Octβ2R. Activation or inhibition of Octβ2R leads to a specific increase or lack of activation, respectively, in PKA and CaMKII activity in the oviduct epithelium.

In certain embodiments Octβ2R antagonist alone or together with OAMB antagonist or with PKA or CaMKII inhibitor can be used to inhibit reproduction of harmful insects. Harmful insects include mosquitoes, fruit flies, and medfly.

Mosquito-borne diseases including malaria, yellow fever, dengue, and West Nile virus are serious health issue. Mosquitoes have an Octβ2R ortholog (as well as OAMB, PKA and CaMKII orthologs as well). Compositions described herein can be used to block egg laying in mosquitoes.

*Drosophila suzukii* (aka Spotted Wing *Drosophila* (SWD)) ovulates on soft-skin fruits and is a detrimental insect in fruit farms. Of particular concern is that its population has been rapidly increasing and spreading. There is no effective strategy to control them.

In certain aspects a Octβ2R angonist alone or together with OAMB agonist or together with PKA or CaMKII activator are used to increase ovulation in beneficial insects. For example the agonist compositions can be administered or put in contact with honeybees to increase reproduction.

The term "isolated" can refer to a compound that is substantially free of cellular material, bacterial material, viral material, culture medium (when produced by recombinant DNA techniques), chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel.

Other embodiments of the invention are discussed throughout this application. Any embodiment discussed with respect to one aspect of the invention applies to other aspects of the invention as well and vice versa. Each embodiment described herein is understood to be an embodiment of the invention that is applicable to other aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figures 1A, 1B:
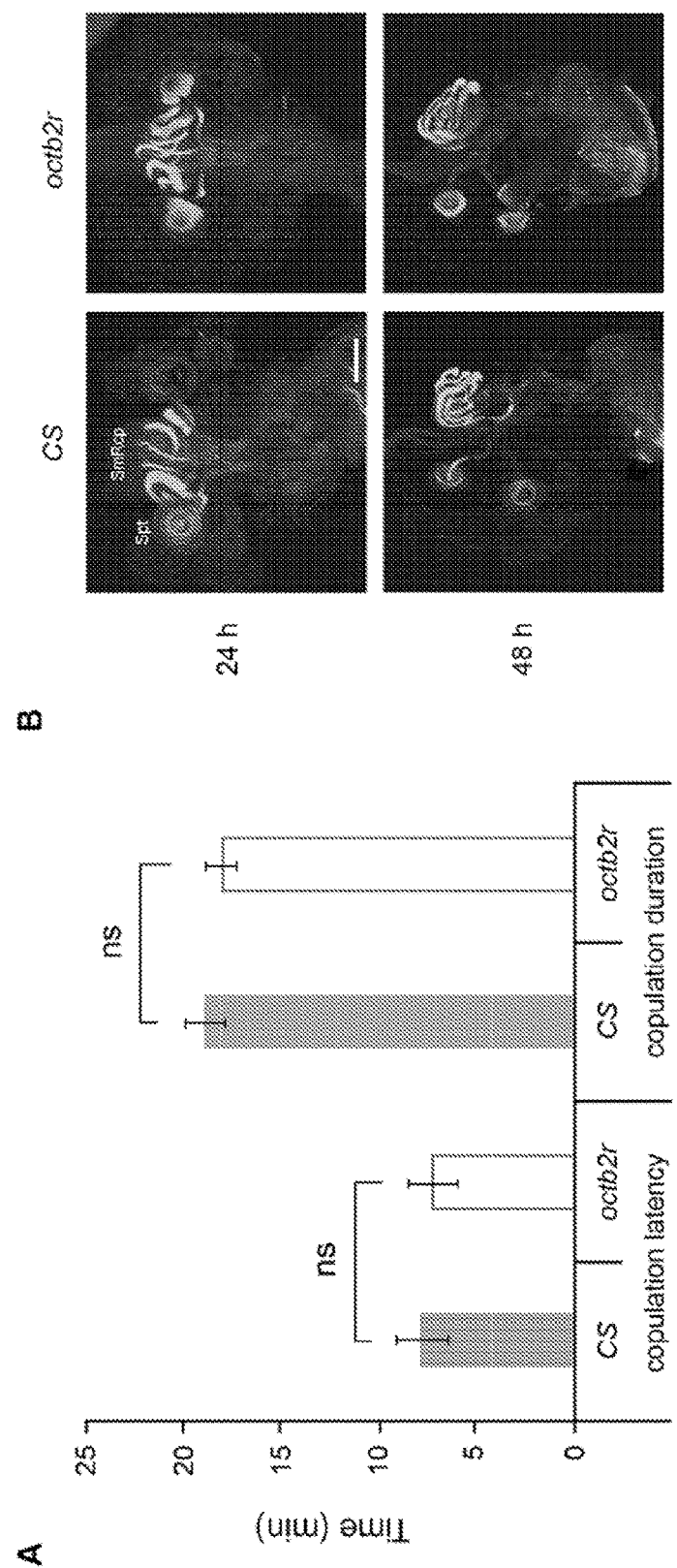
FIG. 1A-1D. The sterility phenotype of the octβ2r mutant female is due to defective ovulation. (A) Copulation behavior—Virgin wild-type CS or octβ2r females were singly paired with naïve CS males to examine copulation behavior. The CS males paired with octβ2r females exhibited copulation latency and duration comparable to those paired with CS females (p>0.05 by Student's t-test; n=17-24). (B) Sperm retention—CS and octβ2r females were mated with dj-GFP males carrying GFP-tagged sperm (green) and the reproductive systems were dissected and counterstained with DAPI (blue). CS and octβ2r females had comparable sperm storage in the seminal receptacle and spermathecae at 24 and 48 h after mating. Spt, spermathecae; SmRcp, seminal receptacle. Scale bar, 50 µm. (C) Ovulation—CS and octβ2r females were mated with CS males and the reproductive systems were dissected to examine the location of the egg in the oviduct or uterus. The octβ2r females had significantly lower levels of ovulation than CS females (***, p<0.0001 by Student's t-tests; n=10). (D) Courtship behavior—Virgin CS and octβ2r females were singly paired with naïve CS males to measure courtship activity. The mated females were tested again with new naïve males 48 h later to measure courtship receptivity. The percentage of time that the CS males spent courting CS or octβ2r females represents courtship index. With both CS and octβ2r females, courtship activities of the males paired with mated females were significant lower than those of the males paired with virgin females (p<0.0001 by Mann-Whitney; n=32-69). Thus, CS and octβ2r females have comparable pre- and post-mating courtship activity. ns, not significant.

Octopamine (β,4-dihydroxyphenethylamine) is an endogenous biogenic amine that is closely related to norepinephrine, and has effects on the adrenergic and dopaminergic systems. It is also found naturally in numerous plants, including bitter orange. OA is used clinically as a sympathomimetic agent under the trade names Epirenor, Norden, and Norfen.

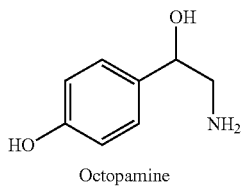 [SMILES: NCC(O)c1ccc(O)cc1]

Octopamine

Oviposition (egg-laying) consists of ovulation, transfer of a mature egg from the ovary to the uterus where fertilization occurs, and deposition of eggs to an external location with proper environmental conditions. Octopamine (OA) is vital for oviposition (Lee et al. Dev. Biol. 2003, 264:179-190; Monastirioti. Dev. Biol. 2003, 264:38-49; Cole et al. J. Biol. Chem. 2005, 280:14948-14955; Rodriguez-Valentin et al. J. Cell. Physiol. 2006, 209:183-198; Middleton et al. BMC Biol. 2006, 4:17; Monastirioti et al. J. Neurosci. 1996, 16:3900-3911). Females lacking the vesicular monoamine transporter (VMAT), which is involved in storage and exocytotic release of biogenic amines, are sterile and the sterility is rescued by transgenic VMAT expression in the OA but not in other biogenic amine neurons in the vmat mutant (Chen et al. Genetics. 2013, 193:159-176). OA is made from tyrosine by the sequential actions of tyrosine decarboxylase (TDC) and tyramine betahydroxylase (TβH), and functions as a neurotransmitter, neuromodulator and neurohormone (Roeder. Annu. Rev. Entomol. 2005, 50:447-477). Similar to the vmat mutant, the tdc2 or tβh mutant females are sterile, and OA feeding in the mated tdc2 or tβh females is sufficient to induce egg-laying (Cole et al. J. Biol. Chem. 2005, 280:14948-14955; Monastirioti et al. J. Neurosci. 1996, 16:3900-3911). While OA neurons have broad projection patterns within and outside of the central nervous system (CNS) (Monastirioti et al. J. Comp. Neurol. 1995, 356:275-287; Sinakevitch and Strausfeld. J. Comp. Neurol. 2006, 494:460-475), the subset of OA neurons in the abdominal ganglion that innervates the reproductive system plays a key role in oviposition since restored TβH expression in those neurons reinstates fecundity of the tβh females (Monastirioti. Dev. Biol. 2003, 264:38-49). In the reproductive system OA axon terminals are found in the ovaries, oviducts, sperm storage organs and uterus where OA is likely to exert multiple functions (Monastirioti. Dev. Biol. 2003, 264:38-49, Cole et al. J. Biol. Chem. 2005, 280:14948-14955; Rodriguez-Valentin et al. J. Cell. Physiol. 2006, 209:183-198; Middleton et al. BMC Biol. 2006, 4:17). For instance OA, when applied to the dissected reproductive system, modulates muscle activity in a tissue specific manner: it enhances muscle contractions in the ovary but inhibits them in the oviduct (Rodriguez-Valentin et al. J. Cell. Physiol. 2006, 209:183-198; Middleton et al. BMC Biol. 2006, 4:17). This suggests that OA receptors present in the ovary, oviduct and other areas regulate distinct elements of the reproductive process.

Five G-protein coupled receptors specific for OA are identified in Drosophila and comprise two alpha1 adrenergic-like receptors OAMB-K3 and OAMB-AS generated from the oamb locus by alternative splicing and three beta adrenergic-like receptors Octβ1R, Octβ2R, and Octβ3R (Han et al. J. Neurosci. 1998, 18:3650-3658; Maqueira et al. J. Neurochem. 2005, 94:547-560; Balfanz et al. J. Neurochem. 2005, 93:440-451). When assayed in cultured cells heterologously expressing these receptors, the alpha-1-like OAMB stimulates the increase in intracellular $Ca^{2+}$ whereas the beta-like receptors increase cAMP levels (Han et al. J. Neurosci. 1998, 18:3650-3658; Maqueira et al. J. Neurochem. 2005, 94:547-560; Balfanz et al. J. Neurochem. 2005, 93:440-451). It has been shown that OAMB in the oviduct epithelium is involved in mediating the octopaminergic signal for ovulation (Lee et al. PLoS One. 2009, 4:e4716). As described herein, the oviduct epithelium requires an additional OA receptor, the beta-like Octβ2R, for ovulation and full fecundity. Also shown is that the downstream effectors of Octβ2R and OAMB have nonoverlapping functions in the oviduct epithelium for fecundity.

Mating activates diverse physiological processes for egg laying in insects. One of the critical processes is to stimulate the oviduct activity facilitating egg transport from the ovary to the uterus since anomalies in this activity lead to infertility. The major insect monoamine OA is an important neuromodulator for ovulation but the underlying mechanism is not yet fully understood. As described herein, the G-protein coupled receptor Octβ2R in the oviduct epithelium is essential for ovulation in Drosophila. The Octβ2R's role in ovulation is physiological, rather than developmental, which is consistent with the finding that feeding OA to the mated tβh mutant females rescues sterility (Monastirioti et al. J. Neurosci. 1996, 16:3900-3911). It has been shown that another OA receptor, OAMB, located in the oviduct epithelium is indispensable for ovulation as well. Thus, OA acts on both alpha1-like OAMB and beta-like Octβ2R to stimulate the oviduct activity critical for ovulation. Since the females with a homozygous mutation in either octβ2r or oamb are sterile, individual Octβ2R or OAMB function in the oviduct epithelium is necessary, but not sufficient, to mediate OA's effects on ovulation.

Figures 5A, 5B:
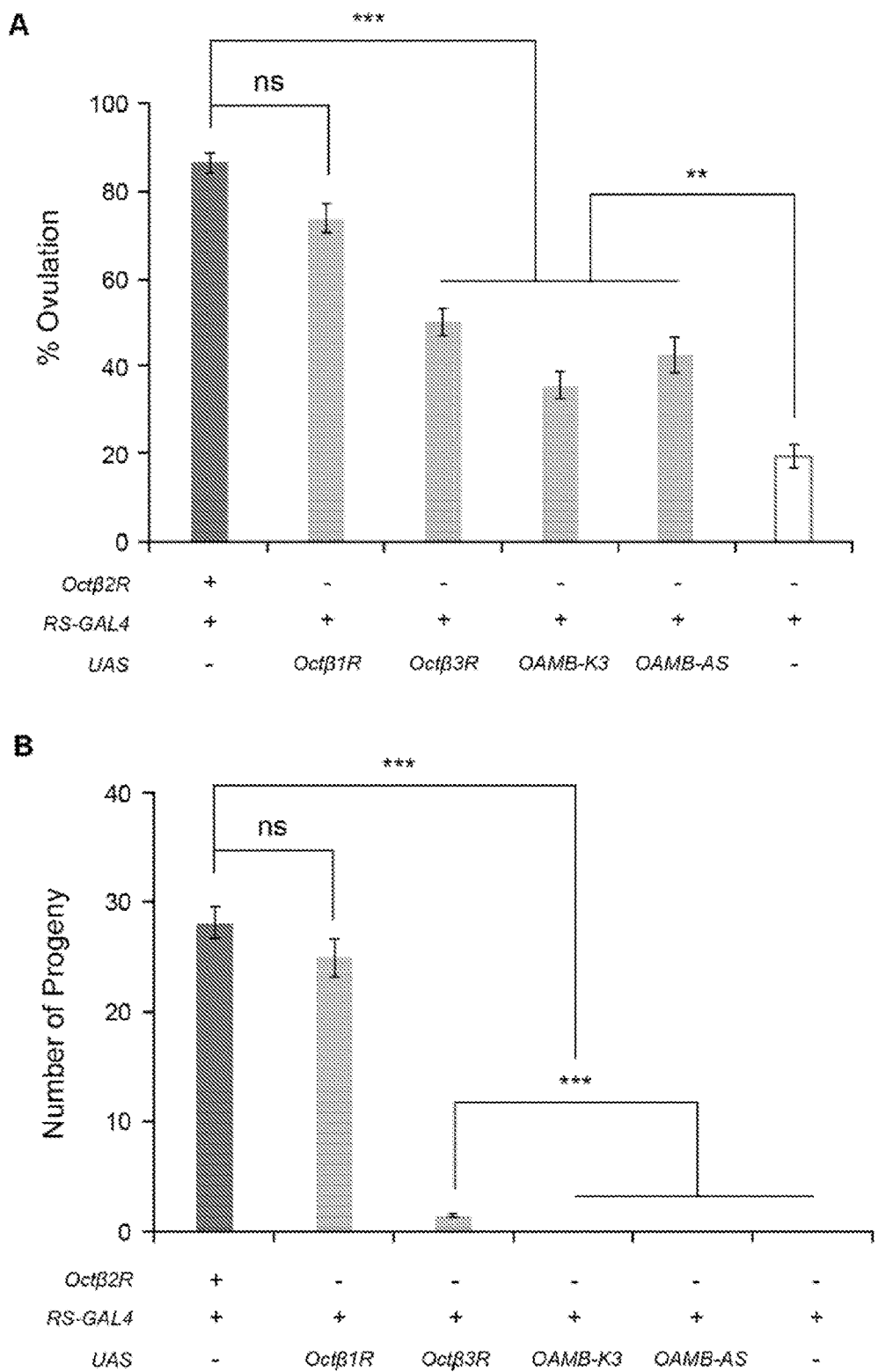
FIG. 5A-5C. Functional substitution by other OA receptors. Transgenic expression of the OA receptors Octβ1R, Octβ3R, OAMB-K3 and OAMB-AS was driven by RS-GAL4 in the octβ2r's oviduct epithelium. (A) Ovulation rescue. Ectopically expressed Octβ1R fully rescued the octβ2r's ovulation phenotype while Octβ3R, OAMB-K3 and OAMB-AS yielded partial rescue (*, p<0.0001; , p<0.005; ns, not significant; n=18-34). (B) Fecundity rescue. Ectopic expression of Octβ1R fully restored fecundity whereas partial or no rescue was observed with ectopic expression of Octβ3R or OAMB-K3 and OAMBAS, respectively (***, p<0.0001, n=20-38). (C) RT-PCR analysis. RNA was isolated from dissected reproductive tissues of CS, octβ2r mutant females carrying RS-GAL4 alone, and octβ2r mutant females carrying RS-GAL4 and UAS-Octβ1R or UAS-Octβ3R for RT-PCR. The elevated levels of Octβ1R or Octβ3R PCR products were detectable in the octβ2r females carrying RS-GAL4 and UAS-Octβ1R or UAS-Octβ3R, respectively. Rp49 was used for an internal control.

OAMB activates CaMKII, but not PKA, for ovulation since ectopic expression of constitutively active CaMKII, but not PKA, fully reinstates ovulation in the oamb mutant ovulation (Lee et al. *PLoS One.* 2009, 4:e4716). In contrast, Octβ2R involves both PKA and CaMKII as downstream signaling molecules. OAMB-K3 stimulates both cAMP and Ca2+ increases in transfected cells (Han et al. *J. Neurosci.* 1998, 18:3650-3658) and in vivo ovulation (Lee et al. *PLoS One.* 2009, 4:e4716, Crocker et al. *Neuron.* 2010, 65:670-681). Since PKA and CaMKII partially rescue the octβ2r's sterility phenotype, the inventor contemplates that OAMB-K3 would offer complete or better rescue than OAMB-AS that increases only Ca2+. Ectopic OAMB-K3 expression, however, led to incompletely rescued ovulation like ectopic OAMB-AS expression and to a lesser extent than ectopic Octβ3R expression (FIG. 5A). This supports the notion that Octβ2R recruits additional effector systems that Octβ1R, but not OAMB-K3 or Octβ3R, can activate for full fecundity. Given that multiple effectors and signaling pathways are recruited for full fecundity, OAMB-AS, OAMB-K3 and Octβ3R may activate only a subset of effectors or signaling pathways that could support ovulation to a limited extent but are insufficient to execute successful egg laying or progeny production.

Figure 7:
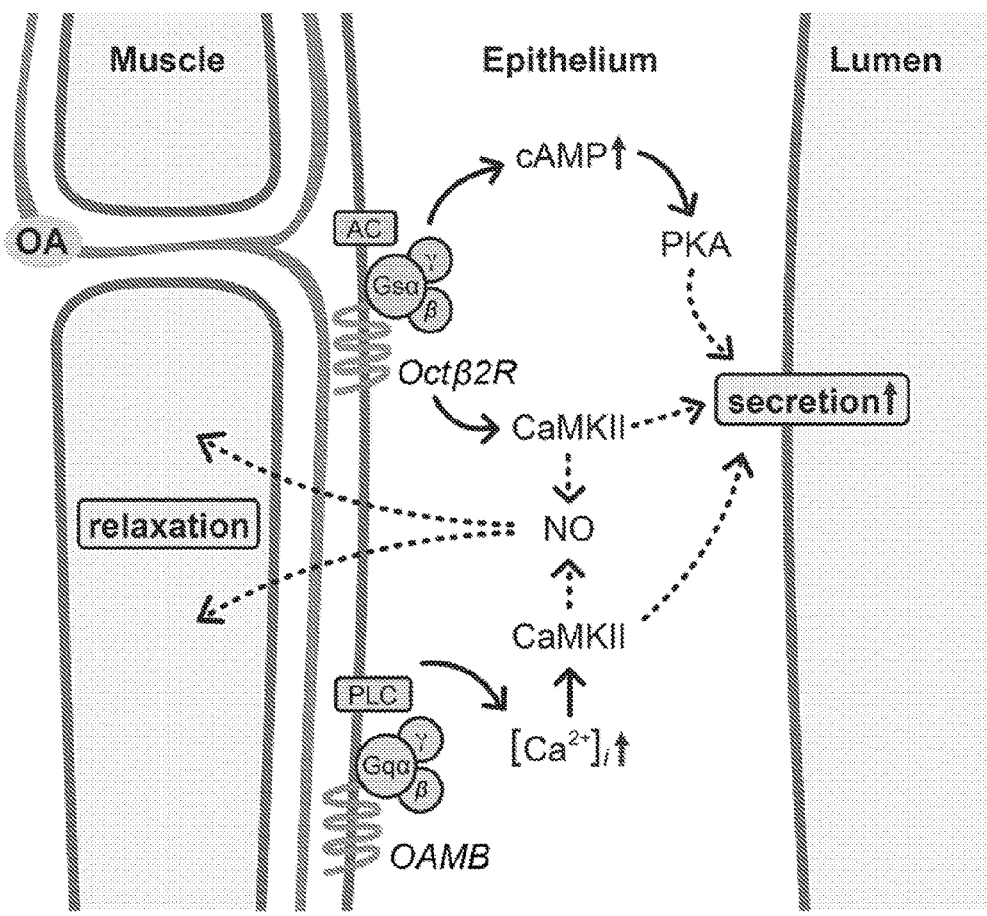
FIG. 7. Working model of ovulation mechanism. Mating activates the OA neurons that project to the oviduct epithelium. Binding of OA to the G-protein coupled receptors Octβ2R and OAMB in the epithelium induces cellular activity critical for egg transport from the ovary to the uterus. Specifically, CaMKII activated by Octβ2R together with OAMB may act on nitric oxide synthase (NOS) to release NO, which diffuses to the muscle for relaxation. Concerted activities of PKA and CaMKII activated by Octβ2R, on the other hand, trigger downstream effectors to secrete fluid for egg activation and transport.

There is no information regarding which downstream molecules of PKA and CaMKII or additional cellular components in the oviduct epithelium are involved in the regulation of the oviduct activity for egg transport. OA relaxes the oviduct muscle when applied to the reproductive system (Middleton et al. *BMC Biol.* 2006, 4:17), however the OA receptor responsible for this action has not been found in the muscle. One explanation is that OA activates Octβ2R and OAMB in the epithelium positioned between the visceral muscle and lumen for dual physiological processes, i.e. oviduct muscle relaxation and fluid secretion to the lumen (FIG. 7). CaMKII activated by OAMB together with Octβ2R may act on nitric oxide synthase (NOS) to release NO, which in turn travels to the muscle for relaxation in a similar mechanism known in other systems (Schneider et al. *Am. J. Physiol. Heart Circ. Physiol.* 2003, 284:H2311-2319; Drazen et al. *Nitric Oxide.* 1999, 3:366-374; Jones et al. *Am. J. Physiol. Heart Circ. Physiol.* 2007, 292:H2634-2642; Agnew et al. *Br. J. Pharmacol.* 2012, 166:327-338). This is supported by the observation that NOS knockdown in the oviduct epithelium significantly reduces ovulation (unpublished data). On the other hand, concerted activities of PKA and CaMKII along with other effectors activated by Octβ2R may be important for fluid secretion to create a suitable chemical environment for egg activation and transport (FIG. 7). This is consistent with the finding that ectopic OAMB-AS expression leads to partially restored ovulation but not to progeny production. Mating induces remodeling of the oviduct epithelium to a fully differentiated morphology (Kapelnikov et al. *BMC Dev. Biol.* 2008, 8:114). It is possible that Octβ2R signaling may be involved in the remodeling process. Alternatively, Octβ2R signaling results in physiological activity of the remodeled epithelium. Ectopic activation of PKA and CaMKII in the wild-type or octβ2r epithelium does not induce ovulation without mating (data not shown).

Most studies in the field of female reproduction have focused on oviposition behavior in an attempt to develop a strategy to lure reproductive females for the management of insect pests and vectors. However, little is known about the physiological and cellular mechanisms mediating the oviposition process. Many functions of OA are conserved in insects. For example, OA plays a pivotal role in reward-mediated olfactory learning in fruit flies, honeybees, and crickets (Zhou et al. *The Journal of neuroscience: the official journal of the Society for Neuroscience.* 2012, 32:14281-14287; Unoki et al. *Eur. J. Neurosci.* 2005, 22:1409-1416; Farooqui et al. *J. Neurosci.* 2003, 23:5370-5380; Kim et al. *Genes Brain Behav.* 2007, 6:201-207; Schwaerzel et al. *J. Neurosci.* 2003, 23:10495-10502). Consistently, OA is implicated in oviposition control in cattle ticks, locust, and cowpeas (Cossio-Bayugar et al. *J. Insect Physiol.* 2012, 58:628-633; Nykamp and Lange. *J. Insect Physiol.* 2000, 46:809-816; Yamane and Miyatake. *J. Insect Physiol.* 2010, 56:271-276; Booth. *Exp. Appl. Acarol.* 1989, 7:259-266) and the counterparts of OAMB and Octβ2R are found in other insects including all other *Drosophila* species, honeybees, silkworms, locust, and mosquitoes (Flybase-Consortium. *Nucleic Acids Res.* 2003, 31:172-175; Evans and Maqueira. *Invert. Neurosci.* 2005, 5:111-118; Wu et al. *J. Exp. Biol.* 2012, 215:2646-2652; Chen et al. *Insect Biochem. Mol. Biol.* 2010, 40:476-486). Enhanced understanding of the mechanism by which OA regulates female fertility would thus help design new strategies to manage beneficial and harmful insects. This study has broader implications as well. Norepinephrine and epinephrine, functional counterparts of OA in vertebrates (Roeder. *Annu. Rev. Entomol.* 2005, 50:447-477; Evans and Maqueira. *Invert. Neurosci.* 2005, 5:111-118), also regulate ovulation in mammals. The adrenergic receptors that norepinephrine and epinephrine activate are found in the human oviduct epithelium although their functions are yet uncharacterized (Helm et al. *Acta Physiol. Scand.* 1982, 114:425-432). Nevertheless, beta-adrenergic agonists induce relaxation of the smooth muscle and stimulate fluid production in the isolated human oviduct (Khan et al. *Pharmacology.* 2005, 74:157-162; Tay et al. *Hum. Reprod.* 1997, 12:2451-2456). Medications commonly used for hypertension, asthma, and depression target adrenergic systems, implicating their potential side effects on reproduction. The information disclosed herein can help understand fertility issues possibly associated with chronic use of adrenergic drugs.

I. OCTβ2R MODULATORS

In certain embodiments an organism can be administered an Octβ2R modulator, either an agonist or an antagonist. In certain aspect an insect is administered an Octβ2R antagonist to inhibit ovulation. In a further aspect, a mammal is administered and Octβ2R agonist to stimulate ovulation.

Octβ2R agonist include, but is not limited to amitraz (N,N'-[(methylimino)dimethylidyne]di-2,4-xylidine), chlordimeform (N'-(4-chloro-2-methylphenyl)-N,N-dimethylmethanimidamide), formetanate (3-((E)-[(Dimethylamino)methylene]amino) phenyl methylcarbamate), and formparanate (4-{[(Dimethylamino)methylene]amino}-3-methylphenyl methylcarbamate).

Oct2R antagonist include, but is not limited to phentolamine or cyproheptadine.

Beta adrenergic receptor agonist include, but is not limited to (R)-4-[1-hydroxy-2-[3,4,5-trimethoxy-phenyl)-ethylamino]-ethyl)-benzene-1,2-diol, (R)-4-[1-hydroxy-2-[3,4,5-trimethoxy-phenyl)-ethylamino]-ethyl)-benzene-1,2-diol hydrochloride, (R)-5-(1-hydroxy-2-[2-(3,4,5-trimethosy-phenyl)-ethylamino]-ethyl)-benzene-1,3-diol, or (R)-5-(1- hydroxy-2-[2-(3,4,5-trimethoxy-phenyl)-ethylamino]-ethyl)-benzene-1,3-diol hydrochloride

II. METHODS OF SCREENING

The methods described herein may employ a reporter gene that confers on its recombinant hosts a readily detectable phenotype. Generally, reporter genes encode a polypeptide not otherwise produced by the host cell, which is detectable by in situ analysis of the cell culture, e.g., by the direct fluorometric, radioisotopic, or spectrophotometric analysis. In certain aspects expression of a reporter gene can be detected in cell culture without the need to remove the cells for signal analysis from the culture chamber in which they are contained. In one example, the gene may encode an enzyme that produces colorimetric or fluorometric change in the host cell which is detectable by in situ analysis and which is a quantitative or semi-quantitative function of cellular or transcriptional activation. Representative examples include cyclases, esterases, phosphatases, proteases, and other enzymes capable of being detected by activity which generates a chromophore or fluorophore as will be known by those individuals having ordinary skill in this art. One well known example is firefly luciferase. Another example is E. coli beta-galactosidase, an enzyme that produces a color change upon cleavage of the indigogenic substrate indolyl-B-D-galactoside by cells bearing beta-galactosidase. Additional example is a green fluorescent protein variant EPAC or GCAM that emits fluorescent at certain wavelength upon binding to cyclic AMP or calcium, respectively.

Another class of reporter genes which confer detectable characteristics on a host cell are those which encode polypeptides, generally enzymes, which render their transformants resistant against toxins, e.g., the neo gene which protects host cells against toxic levels of the antibiotic G418; a gene encoding dihydrofolate reductase, which confers resistance to methotrexate, or the chloramphenicol acetyltransferase (CAT) gene.

In certain aspects methods of screening for agonists of an Octβ2R, comprising the steps of: introducing a reporter construct and an expression construct activated by Octβ2R into a host cell; treating the host cell with potential Octβ2R agonist; and identifying compounds which activate Octβ2R.

In another method of the present invention, one may screen for antagonists of an Octβ2R. This method comprises the steps of: introducing a reporter construct and an Octβ2R activated expression construct into a host cell; pretreating the host cell with an activator of Octβ2R; contacting the host cell with potential antagonists of Octβ2R; and identifying compounds which block the activation of Octβ2R.

The screening methods can use a variety of host cells selected from mammalian cells, such as CV1, HeLa, HepG2, COS, 293, F9, 3T3; or drosophila cells such as Schneider SL2. A person having ordinary skill would readily recognize that other host cell may be used.

The methods can also use an activity assay selected from a luciferase assay, a CAT assay, a beta-galactosidase assay, measuring reporter enzyme levels using such instrument or techniques as luminometer, spectrophotometer and/or thin layer chromatography.

III. INSECT CONTROL FORMULATIONS AND ADMINISTRATION

In certain embodiments, the invention also provides compositions comprising 1, 2, 3 or more insect control agents with one or more of the following: a pharmaceutically acceptable diluent; a carrier; a solubilizer; an emulsifier; a preservative; and/or an adjuvant. Such compositions may contain an effective amount of at least one insect control agent. Thus, the use of one or more insect control agents that are provided herein in the preparation of anti-insect composition is also included. Such compositions can be used to control populations of a variety of insects (class insect). In certain aspects the composition can be used to control insects expressing Octβ2R.

Fruit flies (family Tephritidae) are among the most destructive agricultural pests in the world, destroying citrus crops and other fruit and vegetable crops at an alarming rate and forcing food and agriculture agencies to spend millions of dollars on control and management measures. The term "fruit flies" is used herein to indicate all flies belonging to the family Tephritidae (Diptera), examples of which include *Drosophila suzukii* (Spotted wing *Drosophila*) *Bactrocera dorsalis* (Oriental fruit fly), *Bactrocera cucurbitae* (Melon fly), *Dacus tryoni* (Queensland fruit fly), *Ceratitis capitata* (Mediterranean fruit fly), and fruit flies of the genera *Rhagoletis* and *Anastrepha*, for example. In certain aspects the compositions and methods are for controlling insect of the order Diptera. In a further aspect the insect is of the family Drosophilidae.

The insect control agents may be formulated into compositions in a variety of dosage forms such as, but not limited to, liquid solutions or suspensions, powders, polymeric microcapsules or microvesicles, liposomes, and spray solutions. Formulation components are present in concentrations that are acceptable to the preservation of effectiveness. Buffers are advantageously used to maintain the composition at predetermined pH, typically within a pH range of from about 4.0 to about 8.5, or alternatively, between about 5.0 to 8.0.

Once the composition of the invention has been formulated, it may be stored in vials as a solution, suspension, gel, emulsion, solid, or as a dehydrated or lyophilized powder. Such formulations may be stored either in a ready-to-use form or in a form (e.g., lyophilized) that is reconstituted prior to use.

In one embodiment, the formulation includes an insect control compound described herein in an amount from about 0.01% to about 75% by weight of the total formulation, or any weight range within said weight range. In certain aspects the formulation can include a second insect control composition, e.g., an insecticidal compound. In certain aspect the formulation can include a lure in an amount of from about 0.01% to about 40% by weight of the total formulation, or any weight range within said weight range. For example, in another embodiment, the formulation includes Octβ2R or OAMB receptor antagonist in an amount from about 1% to about 60% by weight of the total formulation and cue lure in an amount of from about 1% to about 30% by weight of the total formulation. In yet another embodiment, the formulation includes Octβ2R or OAMB receptor antagonist in an amount from about 5% to about 45% by weight of the total formulation. In still another embodiment, the formulation includes Octβ2R or OAMB receptor antagonist in an amount from about 10% to about 30% by weight of the total formulation. As used herein, the term "total formulation" refers to all of the ingredients in a given formulation other than water. This term is used in this manner with the understanding that the amount of water included in the emulsion embodiments described herein can vary significantly, which can have an effect on the viscosity of the formulation and the drying time of a coating or dollop of the formulation after application to a locus in the field, but does not otherwise affect the properties or effectiveness of a given formulation. Therefore the values provided in this disclosure as weight percent of a total formulation refer only to the non-water ingredients of the subject formulation.

In an embodiment, the formulation also includes one or more insect toxicant (also referred to herein as an "insecticide," each of these terms being used to include a single insecticide or a combination of more than one insecticide in a given formulation). In one embodiment, the insect toxicant is present in an amount from about 0.002% to about 25% by weight of the total formulation, or any weight range within said weight range. For example, in another embodiment, the formulation includes an insect toxicant in an amount from about 0.01% to about 20% by weight of the total formulation. In yet another embodiment, the formulation includes an insect toxicant in an amount from about 0.1% to about 15% by weight of the total formulation. In still another embodiment, the formulation includes an insect toxicant in an amount from about 0.2% to about 10% by weight of the total formulation.

In one embodiment, the insect toxicant comprises a spinosyn natural factor or semi-synthetic derivative or butenyl-spinosyn natural factor or semi-synthetic derivative. Examples of specific spinosyns that can be used include Spinosad and spinetoram. Spinosad is an insecticide produced by Dow AgroSciences (Indianapolis, Ind.) that comprises approximately 85% spinosyn A and approximately 15% spinosyn D. Spinosyns A and D are natural products produced by fermentation of *Saccharopolyspora spinosa*, as disclosed in U.S. Pat. No. 5,362,634. The spinosyn compounds consist of a 5,6,5-tricylic ring system, fused to a 12-membered macrocyclic lactone, a neutral sugar (rhamnose), and an amino sugar (forosamine). Spinosyn compounds are also disclosed in U.S. Pat. Nos. 5,496,931; 5,670,364; 5,591,606; 5,571,901; 5,202,242; 5,767,253; 5,840,861; 5,670,486 and 5,631,155. As used herein, the term "spinosyn" is intended to include natural factors and semi-synthetic derivatives of the naturally produced factors. A large number of chemical modifications to these spinosyn compounds have been made, as disclosed in U.S. Pat. No. 6,001,981, which is also hereby incorporated by reference.

Spinetoram is a semi-synthetic spinosyn insecticide marketed by Dow AgroSciences LLC. Spinetoram (also known as DE-175) is the common name for a mixture of 50-90% (2R,3aR,5aR,5bS,9S,13S,14R,16aS,16bR)-2-(6-deoxy-3-O-ethyl-2,4-di-O-methyl-α-L-mannopyranosyloxy)-13-[(R2R,5S,6R)-5-(dimethylamino)tetrahydr o-6-methyl-pyran-2-yloxy]-9-ethyl-2,3,3a,4,5,5a,5b,6,9,10,11,12,13,14, 16a,16b-hexadecahydro-14-methyl-1-H-as-indaceno[3,2-d]oxacyclododecine-7,15-dione, and 50-10% (2R,3aR,5aS, 5bS,9S,13S,14R,16aS,16bS)-2-(6-deoxy-3-O-ethyl-2,4-di-O-methyl-α-L-mannopyranosyloxy)-13-[(R2R,5S,6R)-5-(dimethylamino)tetrahydr o-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione. Synthesis of the components of spinetoram is described in U.S. Pat. No. 6,001,981.

In another embodiment, the insect toxicant comprises a macrolide insecticide. Macrolide insecticides related to the spinosyns have been isolated from *Saccharopolyspora* sp. LW107129 (NRRL 30141 and mutants thereof). These compounds are disclosed in U.S. Pat. No. 6,800,614. These compounds are characterized by the presence of reactive functional groups that make further modifications possible at locations where such modifications were not feasible in previously disclosed spinosyns. Natural and semi-synthetic derivatives of the butenyl spinosyns are disclosed in U.S. Pat. No. 6,919,464. The term "butenyl-spinosyn" as used herein is intended to include natural factors and semi-synthetic derivatives of the naturally produced factors.

Spinosyns and butenyl spinosyns are believed to be active against all commercially relevant fruit fly species. Spinosad is approved for use on more than 150 crops. Spinosad has been recognized as an environmentally friendly insecticide, it is used as an organic input and it was a 1999 award winner in the EPAs Presidential Green Chemistry Challenge.

Examples of other insect toxicants that can be used include but are not limited to oranophosphates, such as naled, carbamates, pyrethroids, nicotinics such as imidacloprid or thiacloprid, benzoylphenylureas such as dimilin or novaluron, diacylhydrazines such as methoxyfenozide, phenylpyrazoles such as fipronil or ethiprole, chlorfenapyr, diafenthiuron, indoxacarb, metaflumazone, emamectin benzoate, abamectin, pyridalyl, diamides such as flubendiamide, rynaxypyr (chlorantraniliprole), and cyazypyr (cyantraniliprole), mixes of any of the above or others.

In alternate embodiments, the one or more insect toxicant included in a formulation as described herein can be, for example and without limitation, one or more from the following list: abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, *Bacillus thuringiensis, Bacillus sphaericus*, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-5-methyl, demeton-5-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoatemethyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicam id, flubendiamide (and resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemetonmethyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, Spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, and zolaprofos.

In one embodiment, the insecticide included in the formulation is an insecticide approved for use in organic farming. Organic farming methods are internationally regulated and enforced by many nations, based in large part on standards set by international organizations. Examples of naturally-derived insecticides that have been approved for use on organic farms include, for example, *Bacillus thuringiensis*, pyrethrum, Spinosad, neem, and rotenone.

In addition to the ingredients discussed above, a variety of other ingredients can be incorporated into the insect control formulations as optional additives. Such optional additives include, among others, emulsifiers, plasticizers, volatility suppressants, antioxidants, lipids, various ultraviolet blockers and absorbers, or antimicrobials. In one embodiment, one or more additive is included in the formulation in a total amount of from about 0.001% to about 20% by weight of the total formulation, or any weight range within said weight range.

For example, additional bioactive ingredients can also be included in a formulation as described herein. The term "additional bioactive compound" is used herein to refer to compounds, other than those described above, that fall within one or more of the following categories: attractants, juvenile hormones, plant hormones, pesticides, fungicides, herbicides, nutrients, micronutrients, bacteria (such as *Bacillus thuringiensis*), insect pathogenic virus (such as celery looper virus), fertilizers, plant mineral supplements, or other ingredients that can be included in the formulation to meet specific needs of crop production. For example, the additional bioactive ingredient can include one or more additional male-specific attractants for a variety of additional potential target species, many of which are known and available commercially. Examples include but are not limited to: attractants for Malaysian fruit fly (*Bactrocera latifrons*), including, for example, latilure; for jointed pumpkin fly (*Dacus vertebrates*), including, for example, Verdure; for medfly (*Ceratitis capitata*), including, for example, trimedlure or ceralure; for walnut husk fly (*Rhagoletis completa*), including, for example, alpha copaene; for olive fruit fly (*Bactocera oleae*), including, for example, spiroketal. In one embodiment, one or more additional bioactive ingredient is included in an amount up to about 20% by weight based on the total formulation, or any range within said range.

In yet another embodiment, the formulation also includes a visual attractant, such as, for example a food coloring or other coloring agent, a wide variety of which are known and available commercially. Other ingredients, such as, for example, adjuvants, humectants, viscosity modifiers can also be included.

Another aspect of the present disclosure relates to methods for control and management of fruit flies. Such control is achieved by delivering or applying a formulation as described herein to a locus, such as, for example, a potentially infested area to be protected or an infested area where fruit flies need to be controlled, such as by eradication or the reduction of their numbers to acceptable levels. In one embodiment, the formulation is applied to such area in an amount of from about 0.05 to 1.0 kilograms per hectare. Treatments can include evenly spraying the total amount of product in an area in large dollops (1-4 grams of product) placed on the plants or other surfaces within an orchard. Another manner of treatment includes placing an amount of formulation in traps. Yet another manner of treatment is by spraying or otherwise applying the formulation in an area surrounding an orchard or other area to be treated to avoid leaving residues of formulation components on the crop itself.

In any of the embodiments described herein, the method can include applying an effective amount of the insect control formulation over an area to be treated. In any of the embodiments described herein, the applying can comprise spraying. In any of the methods described herein, the method can include applying the formulation to an area to control fruit flies in an amount sufficient to control such pest. For example the fruit fly species can be any species in the family Tephritidae, such as, for example, a fruit fly species selected from *Bactrocera carambolae*, *Bactrocera caryeae*, *Bactrocera correcta*, *Bactrocera dorsalis*, *Bactrocera invadens*, *Bactrocera kandiensis*, *Bactrocera occipitalis*, *Bactrocera papayae*, *Bactrocera philippinensis*, *Bactrocera umbrosa*, *Bactrocera zonata*, *Bactrocera cucurbitae*, *Bactrocera cucumis*, *Bactrocera tryoni*, and *Bactrocera tau*.

IV. BETA-ADRENERGIC AGONISTS

The methods and compositions described herein can use beta adrenergic agonist to stimulate ovulation in a mammal. In certain aspects the mammal is a human. Beta adrenergic agonists include mixed beta-1/beta-2 agonists or non selective beta agonists, selective beta-1 agonists, or selective beta-2 agonists.

The term "beta adrenergic agonist" as used herein, refers to a drug that activates a beta adrenergic receptor. The terms "beta adrenergic receptor agonist" "beta adrenergic agonist" and "beta agonist" as used herein, are synonymous. A beta adrenergic agonist may be a selective beta-1 adrenergic agonist, a selective beta-2 adrenergic agonist, or a mixed beta-1/beta-2 adrenergic agonist. The term "mixed beta-1/beta-2 agonist" as used herein, refers to a drug that activates both the beta-1 receptor and a beta-2 receptor. It may also be referred to as a non-selective beta agonist.

It will be understood by those of ordinary skill in the art that selective beta-2 agonists may weakly activate the beta-1 receptor and the beta-1 agonists may weakly activate the beta-2 receptor but this weak activation will not be to any significant amount and thus the compound is still classified as a selective beta 1 or beta 2 agonist.

The term "activate" or grammatical variants thereof, as used herein, refers to binding to a receptor and causing the receptor to produce a cellular or physiological change. For example, in one embodiment, a drug that activates a beta adrenergic receptor will cause an increase in the intracellular level of cyclic adenosine monophosphate (cAMP).

Determination if a compound is a beta adrenergic agonist is within the ability of one of ordinary skill in the art. For example, one may utilize the assay as described in U.S. Pat. No. 4,894,219 (the entire disclosure is herein incorporated by reference) to determine if the compound is a beta adrenergic receptor agonist.

Suitable beta adrenergic agonists include, but are not limited to, albuterol, bambuterol, bitolterol, broxaterol, carbuterol, cimaterol, clenbuterol, clorprenaline, colterol, denopamine, dioxethedrine, dopexamine, dopamine, dobutamine, ephedrine, epinephrine, norepinephrine, etafedrine, ethylnorepinephrine, fenoterol, formoterol, hexoprenaline, ibopamine, ibuterol, isoetharine, isoproterenol, isoxsuprine, levabuterol, mabuterol, metaproterenol, methoxyphenamine, oxyfedrine, orciprenaline, picumeterol, pirbuterol, prenalterol, procaterol, protokylol, ractopamine, reproterol, rimiterol, ritodrine, soterenol, salbutamol, salmeterol, terbutaline, tretoquinol, tulobuterol, xamoterol, xinfoate, zinterol, or combinations thereof.

In some embodiments, the beta adrenergic agonist is a selective beta-1 adrenergic agonist, a selective beta-2 adrenergic agonist, or a mixed beta-1/beta-2 adrenergic agonist or a combination thereof.

Examples of selective beta-2 adrenergic receptor agonists include, but are not limited to, metaproterenol, terbutaline, albuterol, isoetharine, pirbuterol, bitolterol, fenoterol, formoterol, procaterol, salmeterol, ritodrine, or a combination thereof.

Examples of selective beta-1 adrenergic receptor agonists include, but are not limited to, dobutamine, noradrenaline, isoprenaline, or a combination thereof. Examples of mixed beta-1/beta-2 agonists include, but are not limited to, isoproterenol, epinephrine, norepinephrine, or combinations thereof.

In various embodiments, because the beta adrenergic receptor agonist is locally or regionally administered (e.g., implanted within 5 cm of the ovaries), therapeutically effective doses may be less than doses administered by other routes (oral, topical, etc.). In turn, systemic side effects, such as for example, liver transaminase elevations, hepatitis, liver failure, myopathy, constipation, etc. may be reduced or eliminated.

In one embodiment, the beta adrenergic agonist is administered in an amount of about 0.0001 mg/kg/day to about 40 mg/kg/day. In another embodiment, the beta adrenergic agonist is administered in an amount of about 0.001 mg/kg/day to about 4 mg/kg/day. In one embodiment, the beta adrenergic agonist is administered in an amount of about 0.01 mg/kg/day to about 0.4 mg/kg/day.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The Octopamine Receptor Octb2R Regulates Ovulation in *Drosophila melanogaster*

The Sterility Phenotype of the Octβ2r Mutant Female.

Figures 1C, 1D:
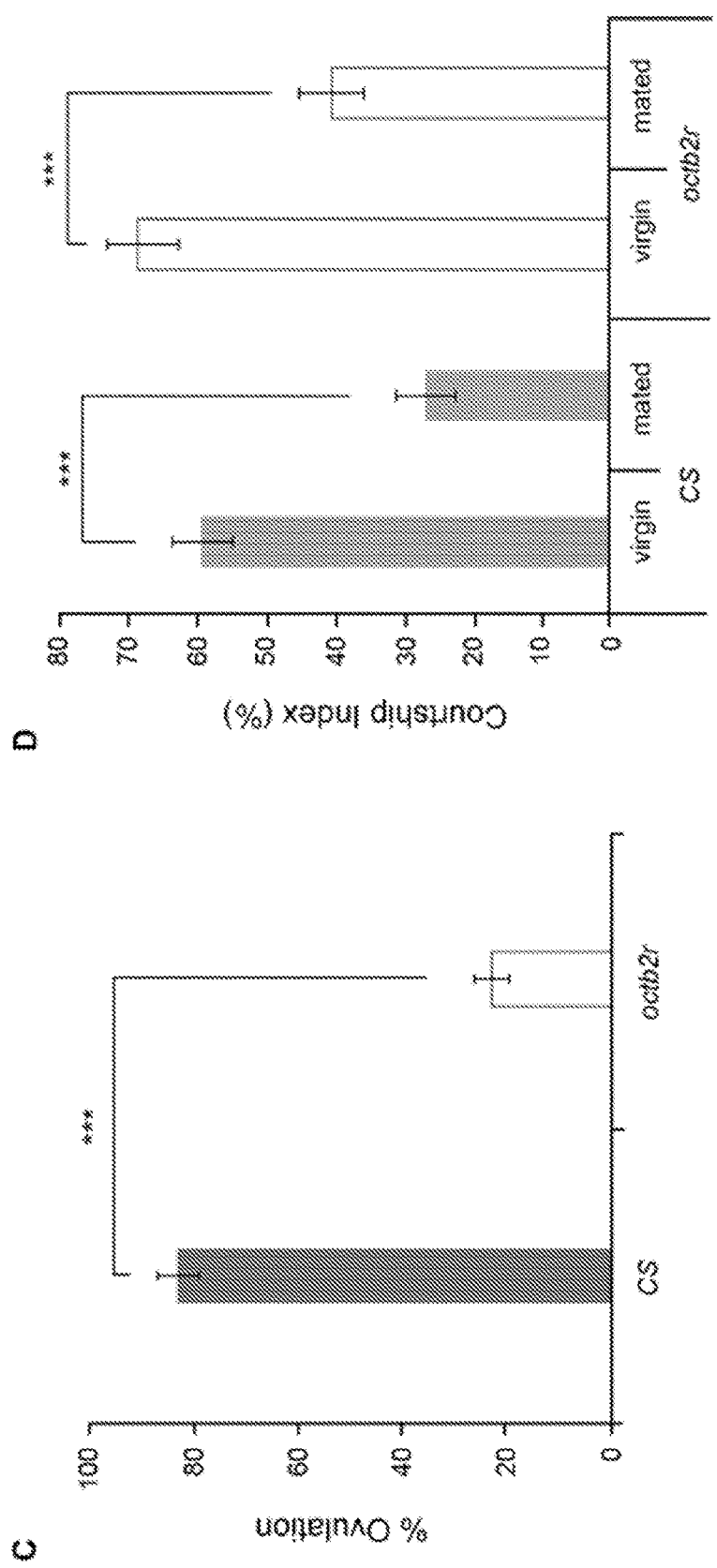

When the octβ2r homozygous mutant flies were housed together, no progeny were detectable. To determine whether females or males contribute to sterility, octβ2r mutant males or females were placed with CS females or males, respectively. While the octβ2r males were fertile (data not shown), the octβ2r females did not produce any progeny. Female fecundity is affected by several behavioral and physiological factors. For example, failure to court or copulate with a male, retain sperm or ovulate and deposit eggs would lead to sterility. When tested with CS males, the octβ2r females had copulation latency and duration times comparable to those of CS females (p>0.05; FIG. 1A). To examine sperm retention, the octβ2r females were mated with dj-GFP males, in which sperm is labeled with GFP. At 24 and 48 h after mating, no anomalies were detectable in the sperm stored in the sperm storage organs, seminal receptacle, and spermathecae (FIG. 1B). Also, there was no ectopically located sperm in other areas of the octβ2r reproductive system. When the reproductive system was examined for ovulation activity, on the other hand, a substantially lower percentage of octβ2r females had an egg in the oviduct or uterus at 18 h post mating compared to CS females (p<0.0001; FIG. 1C). This suggests that impaired ovulation is responsible for the octβ2r's sterility phenotype.

Ovulating female flies are reluctant to re-mate and thus show rejection behavior to courting males, leading to decreased courtship activity by the rejected males. Previous studies show that the females defective in ovulation are also impaired in post-mating rejection behavior (Aigaki et al. *Neuron.* 1991, 7:557-563; Yapici et al. *Nature.* 2008, 451: 33-37; Yang et al. *Neuron.* 2009, 61:519-526; Hasemeyer et al. *Neuron.* 2009, 61:511-518; Rezaval et al. *Current Biology.* 2012, 22:1155-1165). The octβ2r mutant females were studied to determine if they have similar phenotypes by testing their courtship activity with CS males. As shown in FIG. 1D, CS males exhibited significantly less courtship activity with mated CS females than with virgin CS females as predicted (p<0.0001). Likewise, CS males paired with mated octβ2r females showed reduced courtship compared to those paired with virgin octβ2r females (p<0.0001) and none of the mated octβ2r females were engaged in copulation. When CS males' courtship activities toward virgin CS vs. octβ2r females or mated CS vs. octβ2r were examined, no difference was observed (FIG. 1D, p>0.05), supporting that the octβ2r females have normal courtship and rejection behavior. Taken together, these observations indicate that Octβ2R is essential for ovulation but dispensable for pre- and post-mating behaviors.

Octβ2R's Functional Site in Ovulation.

Figures 2A, 2B, 2C, 2D:
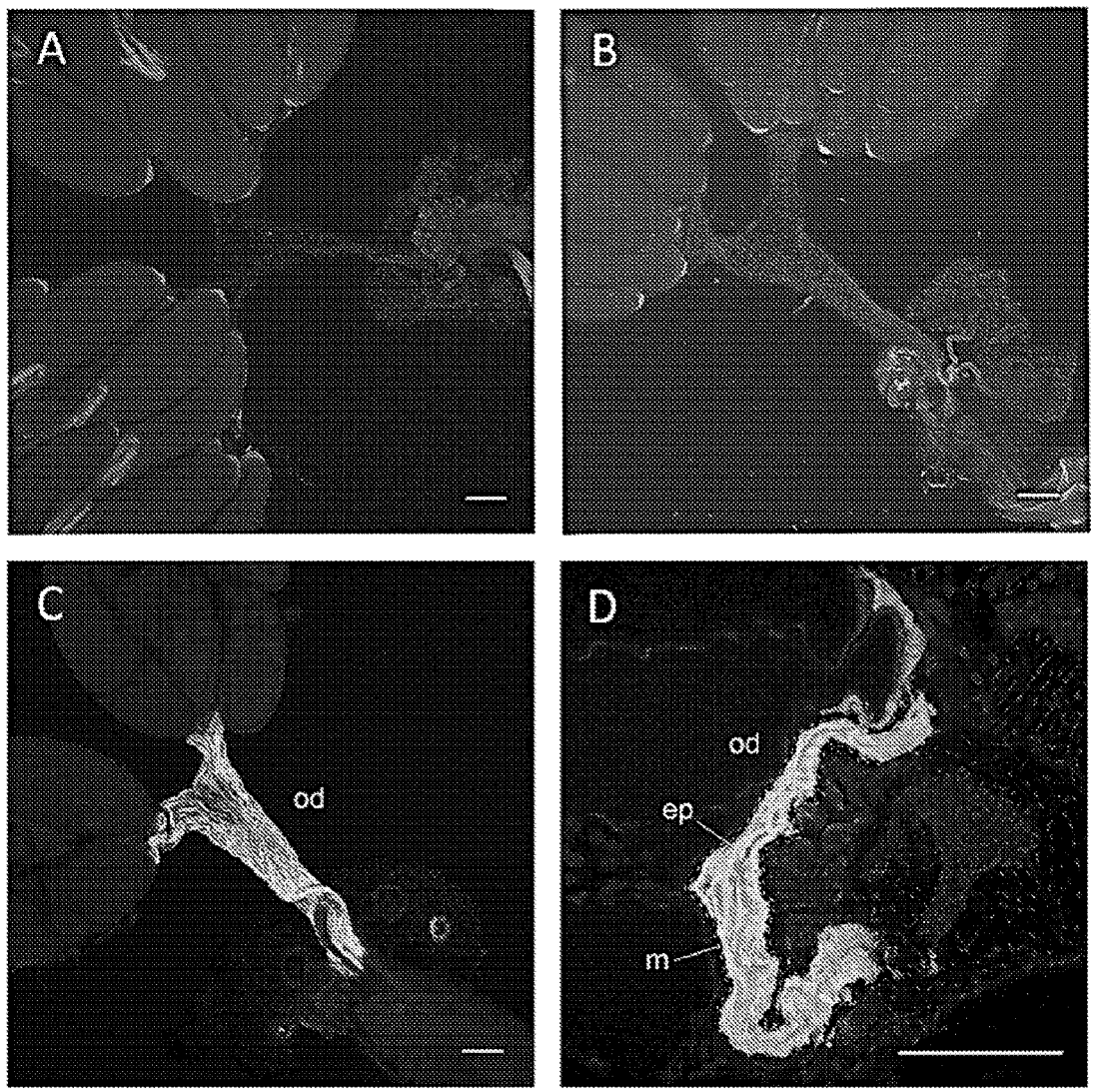
FIG. 2A-2D. Octβ2R expression in the oviduct epithelium. (A) CS. (B) octβ2r carrying UAS-Octβ2R-GFP. (C, D) octβ2r carrying RS-GAL4 and UAS-Octβ2R-GFP. The whole mount (A-C) and cryosectioned (D) female reproductive systems were counterstained with DAPI (blue). Octβ2R-GFP (green) expression is clearly visible in the oviduct epithelium, but not in other areas, of the octβ2r female carrying RS-GAL4 and UASOctβ2R-GFP (C, D). od, oviduct; ep, oviduct epithelial layer; m, oviduct muscle layer demarcated with dashed lines. Scale bars, 100 µm.
Figures 3A, 3B:
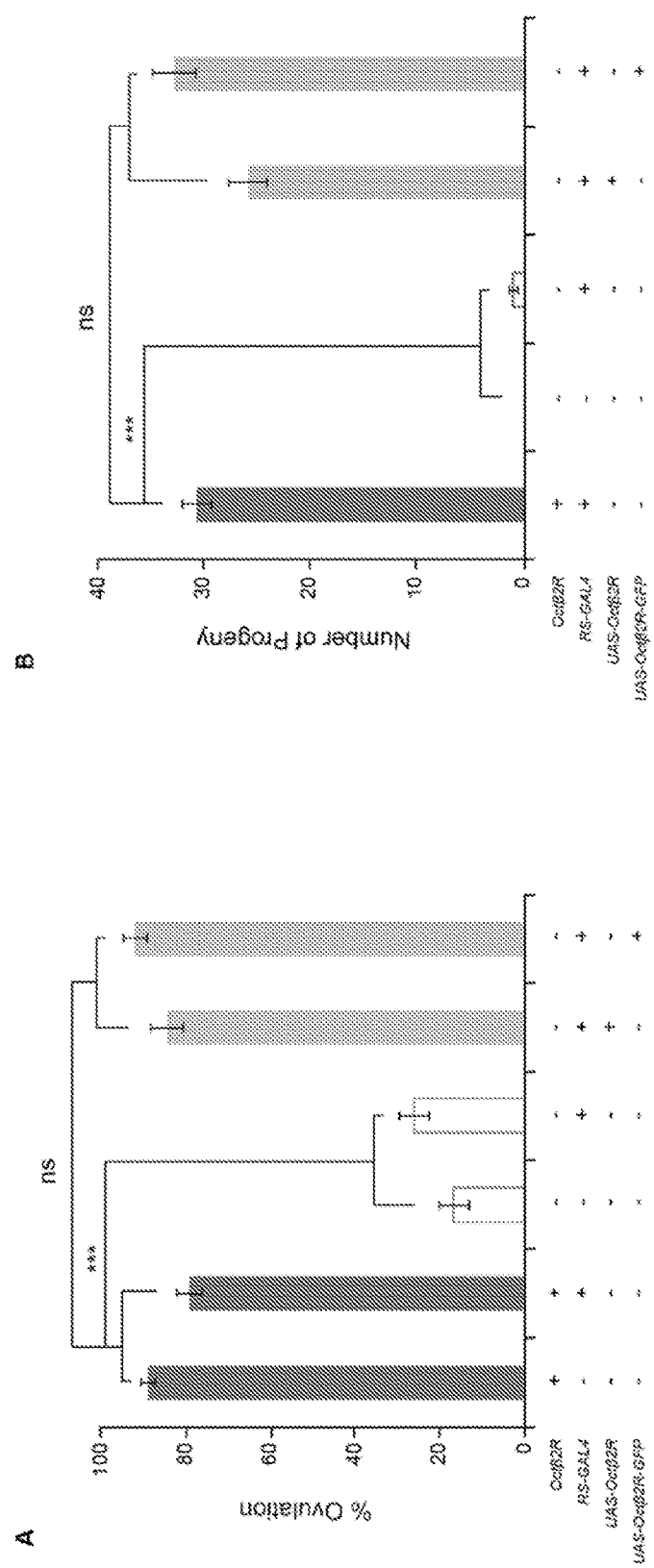
FIG. 3A-3E. Restored Octβ2R expression in the oviduct epithelium rescues the octβ2r's ovulation and fecundity phenotypes. (A, B) Epithelial rescue. The octβ2r females carrying RS-GAL4 and either UAS-Octβ2R or UAS-Octβ2R-GFP had ovulation (A) and fecundity (B) levels comparable to those of CS females (ns, p>0.05; *, p<0.0001; n=17-24 for ovulation tests; n=18-39 for fecundity tests. (C, D) Neuronal rescue. The octβ2r females carrying the pan-neural driver elav-GAL4 or nSyb-GAL4 along with either UAS-Octβ2R or UAS-Octβ2R-GFP exhibited ovulation (C) and fecundity (D) levels comparable to those of the octβ2r mutant females. *, p<0.0001; n=12-27 for ovulation tests; n=15-37 for fecundity tests. (E) Temporal rescue. The females reared at the non-permissive temperature were subjected to heat shock (+HS) to induce Octβ2R expression or kept at non-permissive temperature (-HS) as a noinduction control. The octβ2r females carrying HS-GAL4 and UAS-Octβ2R-GFP treated with heat shock displayed ovulation levels similar to CS (ns, p>0.05; n=13-30) while the females of the same genotype without heat shock showed the ovulation levels significantly different from CS females (***, p<0.0001). In the graph table, "+" denotes the presence of one normal octβ2r allele (heterozygous octβ2r) or a single copy of transgenes except for the first row, which represents wild-type CS with two normal octβ2r alleles, and "-" denotes the absence of normal octβ2r alleles or transgenes.
Figures 3C, 3D:
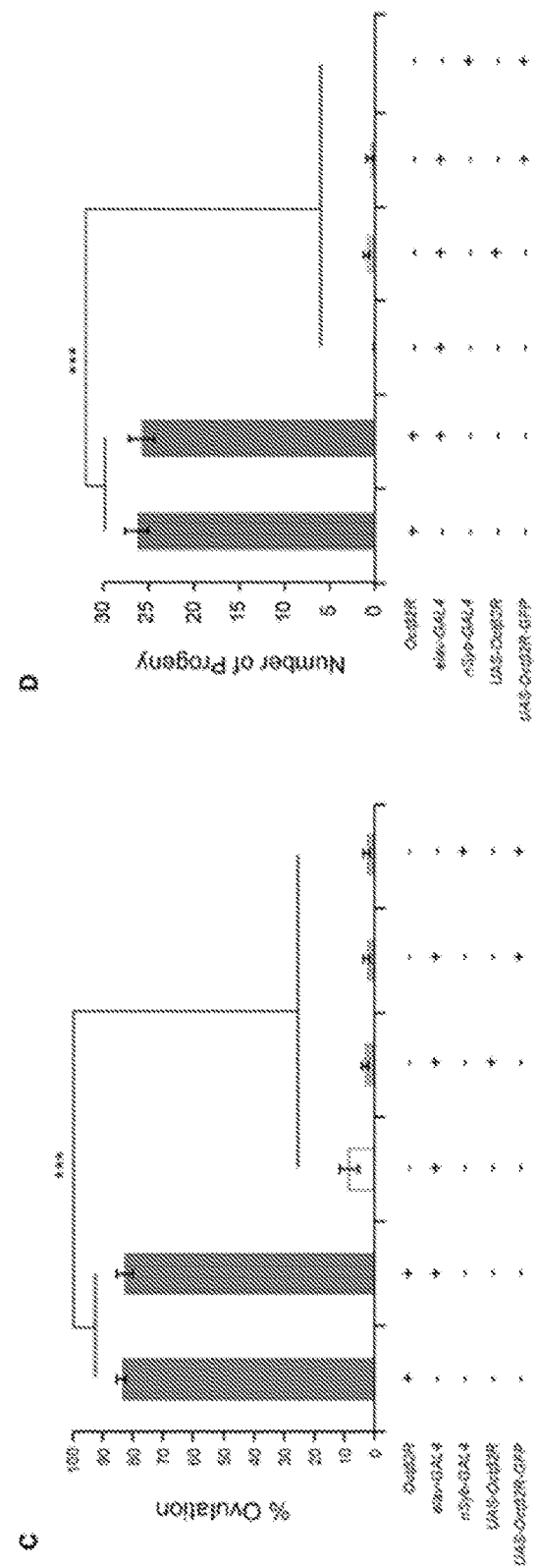

OA containing axons are present in the CNS as well as the reproductive system, thus the site of the OA receptor Octβ2R's function in ovulation could be the CNS neurons controlling ovulation or the reproductive tissue directly involved in ovulation. The microarray and RNA-seq analyses (Flybase-Consortium. *Nucleic Acids Res.* 2003, 31:172-175) show that Octβ2R is expressed at very low levels in the CNS and reproductive tissue, which we also observed with quantitative RT-PCR (data not shown). It has been shown that OA neurons in the abdominal ganglion innervate the oviduct epithelium where alpha1 adrenergic-like OAMB is involved in ovulation (Lee et al. *PLoS One.* 2009, 4:e4716). To identify the site of the Octβ2R's action, the GAL4/UAS binary system was used, in which the transcription factor GAL4 binds to UAS to activate the downstream gene expression (Brand and Perrimon. *Development.* 1993, 118: 401-415). For tissue-specific expression pan-neuronal drivers elav-GAL4 and nSyb-GAL4 were used, and the reproductive system driver RS-GAL4 that has no neuronal expression (Lee et al. *PLoS One.* 2009, 4:e4716). The fusion construct Octβ2R-GFP was also used, in which GFP is fused to the C-terminus of Octβ2R, to monitor the site and level of transgene expression. When driven by RS-GAL4, Octβ2R-GFP was conspicuously visible in the oviduct epithelium but not in the oviduct muscle and ovaries (FIG. 2). The transgenic octβ2r females with RS-GAL4 and UAS-Octβ2R or UAS-Octβ2R-GFP exhibited ovulation and fecundity to the levels significantly different from the octβ2r females (p<0.0001) but comparable to those of the control females (p>0.05; FIGS. 3A and 3B). On the contrary, the octβ2r females carrying the neuronal driver elav-GAL4 and UAS-Octβ2R or UAS-Octβ2R-GFP showed the similar ovulation and fecundity levels as the octβ2r females (p>0.05) and the same results were obtained when another neuronal driver or nSyb-GAL4 was used (FIGS. 3C and 3D). These observations indicate that the oviduct epithelium is a critical site of the Octβ2R's function in ovulation and the nervous system is spared in this process.

Figure 3E:
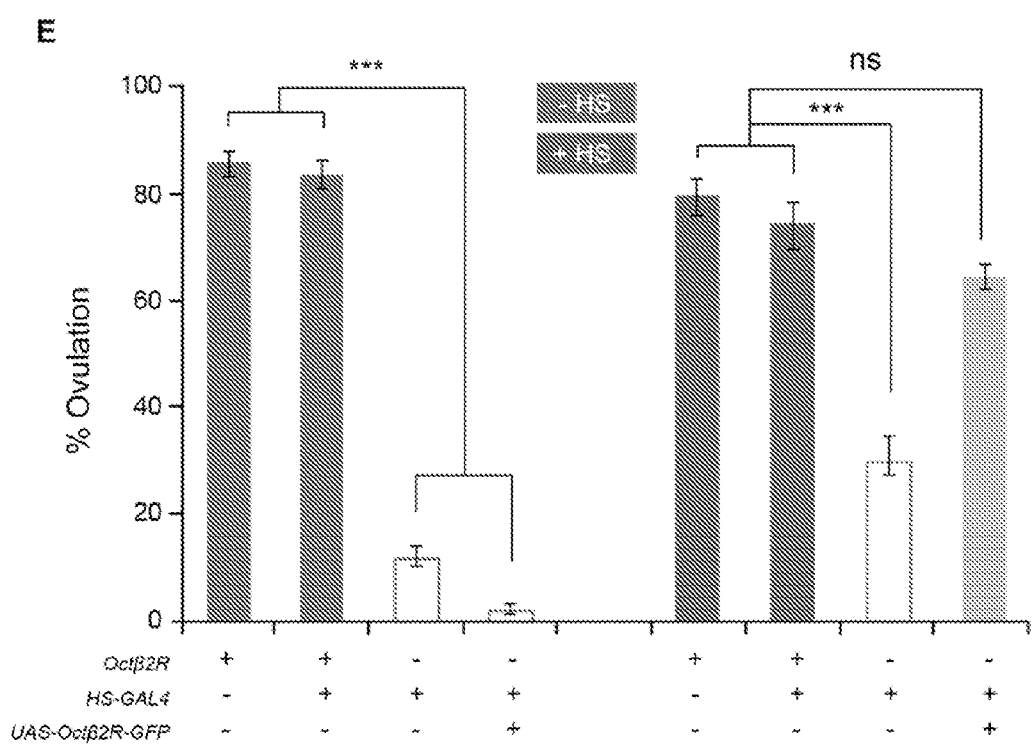

The involvement of Octβ2R in a developmental or physiological process for ovulation was studied. HS-GAL4 was used, in which GAL4 expression is controlled by the heat-inducible hsp70 promoter (Flybase-Consortium. *Nucleic Acids Res.* 2003, 31:172-175), to induce Octβ2R expression upon simple temperature shift. The octβ2r females carrying HS-GAL4 and UAS-Octβ2R-GFP as well as the control females were subjected to heat treatment at 37° C. (FIG. 3E, +HS) and then allowed to mate with CS males at room temperature. Another group of females with the same genotypes that did not receive heat treatment (−HS) was used as an uninduced control. When tested for ovulation, the octβ2r females with HS-GAL4 and UAS-Octβ2RGFP showed a heat-shock dependent rescue of the ovulation phenotype (FIG. 3E). This study suggests a physiological, rather than developmental, role of Octβ2R in ovulation.

Downstream Effectors of Octβ2R.

Figures 4A, 4B:
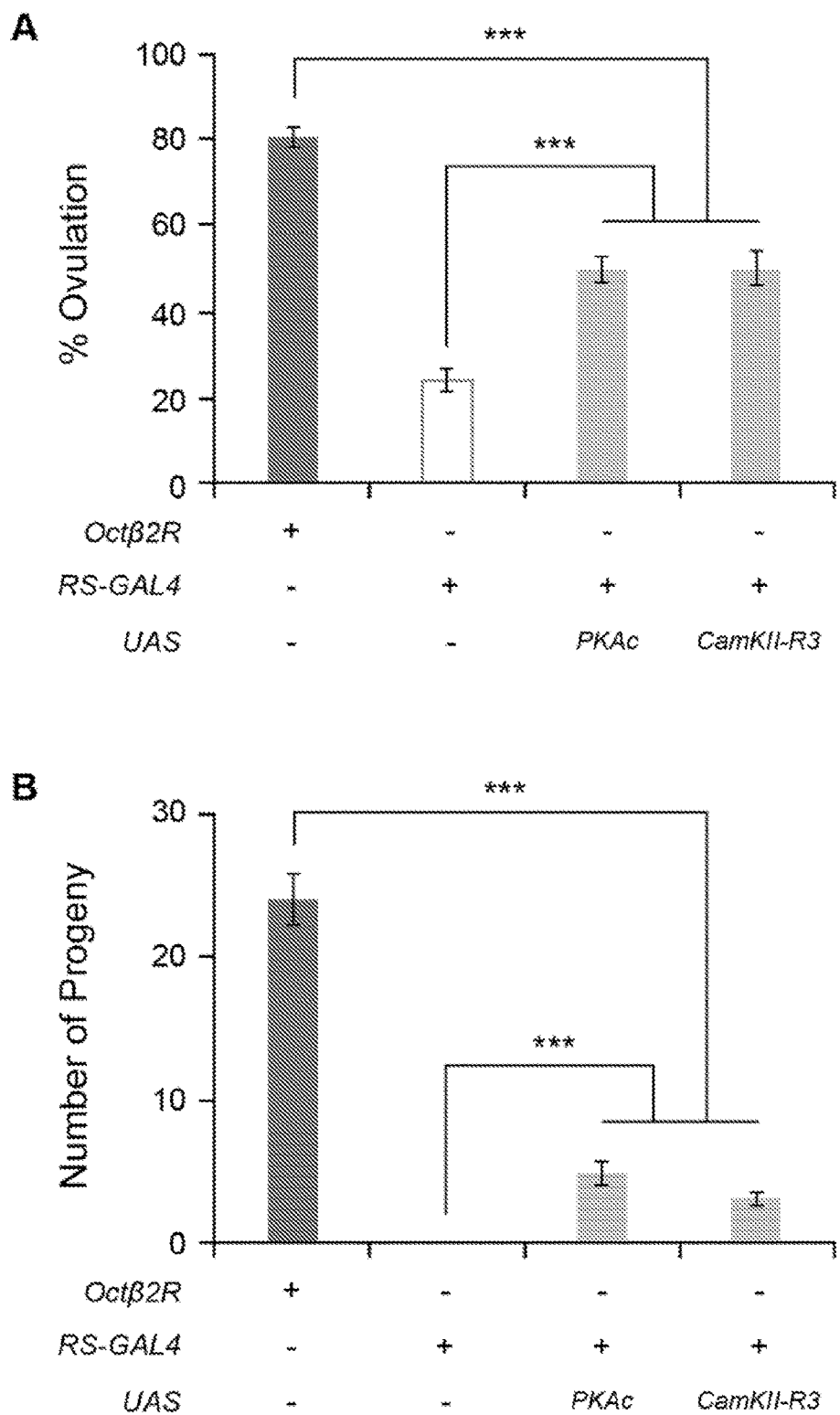
FIG. 4A-4B. Octβ2R activates both PKA and CaMKII in the oviduct epithelium for 27 ovulation and fecundity. Ectopic expression of PKAc or CaMKII-R3 was induced with RS-GAL4 in the oviduct epithelium of the octβ2r mutant females. The octβ2r females carrying RS-GAL4 along with UAS-PKAc or UAS-CaMKII-R3 partially rescued the octβ2r's ovulation (A) and fecundity (B) phenotypes (***, p<0.0001, n=21-26 for ovulation tests, n=21-38 for fecundity tests).

Octβ2R is a G-protein coupled receptor. Thus, a physiological role for Octβ2R after binding to OA is likely to involve the activation of intracellular signaling pathways, which in turn trigger epithelial cell activity facilitating egg delivery from the ovary to the uterus. In an effort to elucidate the cellular mechanism responsible for this activity, downstream molecules mediating Octβ2R's effect on ovulation have been investigated. This study was focused on the protein kinases that functionally interact with Octβ2R in the oviduct epithelium. As noted, Octβ2R stimulates cAMP production in transfected cells, making cAMP-dependent protein kinase A (PKA) an excellent candidate to serve as a downstream effector of Octβ2R. PKA activity is normally repressed in the absence of cAMP since the catalytic subunit is bound to the regulatory subunit. Upon binding of cAMP to the regulatory subunit, the catalytic subunit is released to act on its substrates. If PKA is indeed a downstream effector of Octβ2R in the oviduct epithelium, it was reasoned that activation of PKA in a cAMP-independent manner would bypass Octβ2R and stimulate ovulation in the octβ2r mutant females. To induce cAMP-independent PKA activation, the catalytic subunit of PKA (PKAc) was overexpressed (Kiger et al. *Genetics.* 1999, 152:281-290). Consistent with the notion, the octβ2r females overexpressing PKAc in the oviduct epithelium had significantly higher levels of ovulation (p<0.0001) and fecundity (p<0.0001) than those of the octβ2r females (FIGS. 4A and 4B). The levels, however, were significantly lower than those in the control CS females (p<0.0001), indicating incomplete rescue. These data corroborate PKA as a key downstream effector of Octβ2R in the oviduct epithelium. Incomplete rescue could be due to an insufficient transgene level or an additional effector(s) required for successful ovulation.

Ca2+/calmodulin-sensitive protein kinase II (CaMKII) is important for ovulation since inhibition of CaMKII decreases ovulation (Lee et al. *PLoS One.* 2009, 4:e4716). Whether CaMKII acts downstream of Octβ2R to regulate ovulation was tested. Ectopic expression of the CaMKII-R3 isoform in oviduct epithelial cells resulted in partially restored ovulation and fecundity in the octβ2r females to the levels comparable to those of PKAc overexpression (FIGS. 4A and 4B). This suggests that CaMKII may serve as an additional downstream effector of Octβ2R. Conversely, overexpressed CaMKII may induce an alternative pathway to compensate for deficient Octβ2R signaling. To test this, alpha1-like OAMB receptors were studied, which activate CaMKII in the oviduct epithelium, as to whether they could rescue the octβ2r's sterility phenotype. When ectopically expressed in the oviduct epithelium of the octβ2r female, both OAMB-K3 and OAMB-AS reinstated ovulation to a limited extent like overexpressed PKAc or CaMKII-R3 (FIG. 5A) but did not rescue fecundity (FIG. 5B). These observations suggest that reinstated ovulation conferred by overexpressed CaMKII may be attributable to compensatory activity of the OAMB pathway; on the contrary, rescued fecundity conferred by overexpressed CaMKII is likely independent of the OAMB signaling.

Genetic Interaction of Octβ2R and OAMB.

Figures 6A, 6B:
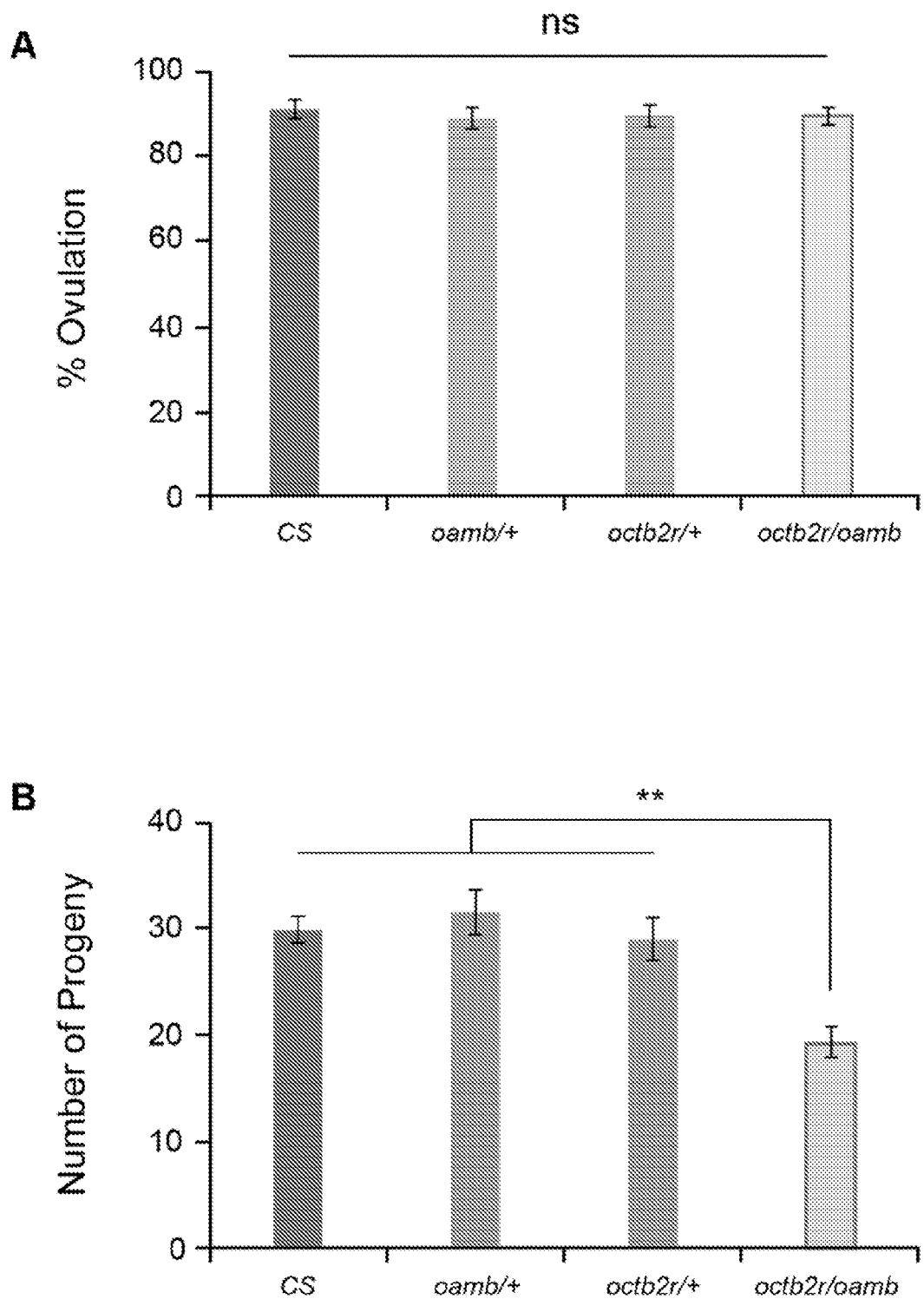
FIG. 6A-6B. Genetic interaction. The heterozygous octβ2r and oamb286 mutant females having two normal alleles of oamb and octβ2r, respectively, and the transheterozygous octβ2r/oamb286 females were tested for ovulation (A) and fecundity (B). While the heterozygous octβ2r and oamb286 females showed normal ovulation and fecundity, the transheterozygous octβ2r/oamb286 females exhibited ovulation comparable to CS (A; ns, p>0.05; n=20) but significantly reduced fecundity (p<0.001; n=21-22).

At present, there is no information available regarding which downstream molecules of PKA and CaMKII or other effectors of Octβ2R and OAMB mediate ovulation and fecundity. As noted a homozygous mutation in either octβ2r or oamb causes sterility (this study and (Lee et al. *Dev. Biol.* 2003, 264:179-190)), thus both Octβ2R and OAMB signals are required for molecular and cellular activities essential for female fertility. In order to elucidate relative contributions of Octβ2R and OAMB signaling to ovulation and fecundity, the genetic interaction of octβ2r and oamb heterozygous mutations was examined. The heterozygous octβ2r or oamb mutant females with normal oamb or octβ2r alleles, respectively, exhibited the ovulation and fecundity levels comparable to those of CS females (p>0.05, FIGS. 6A and 6B). The females with heterozygous mutations in both octβ2r and oamb also had normal ovulation (FIG. 6A) but reduced fecundity (p<0.001, FIG. 6B). These data suggest that the downstream molecules of Octβ2R and OAMB critical for ovulation are somewhat redundant or overlapping, which is consistent with the result that overexpressed OAMB partly compensates for deficient Octβ2R signaling for ovulation (FIG. 5A). On the other hand, the downstream molecules of Octβ2R and OAMB likely have non-redundant or dosage-sensitive functions for fecundity. This is in line with the fact that homozygous mutations in either octβ2r or oamb cause sterility.

Functional Substitution by Other OA Receptors.

Figure 5C:
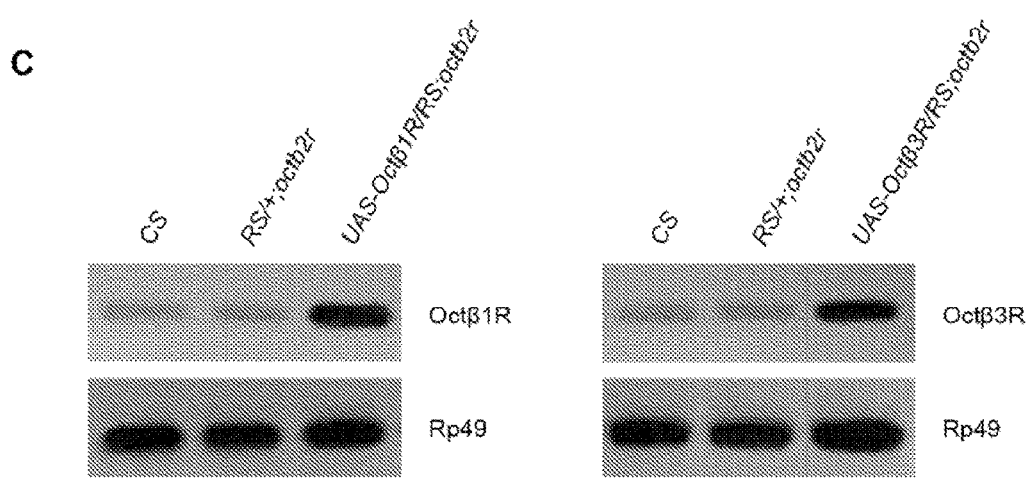

*Drosophila melanogaster* has two additional beta adrenergic-like receptors Octβ1R and Octβ3R and they activate increases in cAMP levels when assayed in heterologous cell lines (Maqueira et al. *J. Neurochem.* 2005, 94:547-560). There is no information regarding their signaling properties in vivo. The inventor contemplates that Octβ1R and Octβ3R would functionally substitute Octβ2R if they have similar signaling capacities in vivo. To test this, octβ2r females were generated carrying RS-GAL4 along with UAS-Octβ1R or UAS-Octβ3R and examined them for fertility. Ectopically expressed Octβ1R in the oviduct epithelium fully reinstated ovulation and fecundity in the octβ2r females (p<0.0001, FIGS. 5A and 5B). However, Octβ3R yielded only partial restoration of ovulation and fecundity to the levels significantly higher than those of octβ2r (p<0.0001) but lower than those of control females (p<0.0001, FIGS. 5A and 5B). In transfected cells, Octβ1R and Octβ3R have a higher or similar potency, respectively, compared to Octβ2R in stimulating cAMP increases (Maqueira et al. *J. Neurochem.* 2005, 94:547-560) while their capacities to activate CaMKII are unknown. Different efficacies of Octβ1R, Octβ3R, and OAMB-K3 to rescue the octβ2r phenotypes could be due to distinct signaling capacities of the OA receptors in vivo. Alternatively, expression levels of the transgenic receptors driven by RS-GAL4 could be insufficient to provide full rescue. RS-GAL4 is a strong driver since RS-GAL4-induced GFP, OAMB-AS, OAMB-K3, or Octβ2R-GFP expression is readily detectable and present at high levels in the oviduct epithelium ((Lee et al. *PLoS One.* 2009, 4:e4716) and FIG. 2). Nonetheless, it is possible that RS-GAL4-driven Octβ3R expression may not be sufficient to fulfill Octβ2R's function deficient in the octβ2r females. Since Octβ1R and Octβ3R antibodies are unavailable, RT-PCR was performed to examine transcript levels in the reproductive system of the octβ2r females carrying RS-GAL4 along with UAS-Octβ1R or UAS-Octβ3R. As shown in FIG. 5C, Octβ1R and Octβ3R RNAs were found in the CS and octβ2r reproductive tissues and present at elevated levels in RSGAL4/UAS-Octβ1R; octβ2r and RS-GAL4/UAS-Octβ3R; and octβ2r, respectively. Relative abundance was examined by real time RT-PCR using two different primer sets for each receptor. Octβ1R and Octβ3R transcript levels in reproductive tissues of the octβ2r females carrying RS-GAL4 and UAS-Octβ1R or UAS-Octβ3R were 21.9 2.3 and 3.2 0.7 folds higher than those in the octβ2r reproductive tissue, respectively. The lower level of Octβ3R compared to Octβ1R transcripts may explain partial rescue. It remains to be resolved whether protein levels of the receptors correspond to the mRNA levels to substantiate the notion.

*Drosophila* Strains and Culture.

All flies, unless otherwise stated, were raised in the standard yeast/cornmeal/agar medium at 25° C. with 50% relative humidity and on a 12-h light-dark cycle. Canton-S (CS) was used as a wild-type strain. The octβ2r mutant used in this study is the transgenic line octβ2rf05679 generated by the Gene Disruption Project (Flybase-Consortium. *Nucleic Acids Res.* 2003, 31:172-175). octβ2rf05679 contains the piggyBac transposon inserted in the 5th exon of the octβ2r gene in the third chromosome, interrupting the coding sequence (Flybase-Consortium. *Nucleic Acids Res.* 2003, 31:172-175), thus likely represents a hypomorphic or possibly null allele (Crocker et al. *Neuron.* 2010, 65:670-681). octβ2rf05679 (hereafter octβ2r) was obtained from the Bloomington Stock Center (stock no. 18896) and backcrossed with Cantonized w1118 for six generations. The oamb mutant used in this study is the null allele oamb286 (Lee et al. *Dev. Biol.* 2003, 264:179-190). Heat shock (HS)-GAL4 (stock no. 2077), elav-GAL4 (stock no. 8765), UAS-CaMKII-R3 (stock no. 29662) and don juan (dj)-GFP (stock no. 5417) flies were obtained from the Bloomington Stock Center, UAS-PKAc from Dr. Kalderon (Columbia University, New York, N.Y.) and nSyb-GAL4 from Dr. Ordway (Pennsylvania State University, State College, Pa.). The RS-GAL4, UAS-OAMB-K3 and UAS-OAMB-AS lines are described in Lee et al. (Lee et al. *PLoS One.* 2009, 4:e4716; Kim et al. *J. Neurosci.* 2013, 33:1672-1677). Individual transgenes (HS-GAL4, elav-GAL4, nSyb-GAL4, RS-GAL4, UAS-OAMB, UAS-PKAc and UAS-CaMKII-R3) were placed in the octβ2r mutant background for rescue experiments.

UAS-OctβR Transgenic Flies.

Octβ1R, Octβ2R, and Octβ3R cDNAs containing the open reading frame (Maqueira et al. *J. Neurochem.* 2005, 94:547-560) were cloned under UAS in the gateway vector pTW (Akbari et al. *BMC Cell Biol.* 2009, 10:8). In addition, Octβ2R was cloned in pTWG, which allows GFP to be fused to the C-terminus of Octβ2R, for monitoring receptor expression and localization. The cloned receptors were injected into w1118 embryos, and germ-line transformed lines were outcrossed with Cantonized w1118 for six generations to normalize the genetic background and cross out potential second site mutations. The transgenes were then placed in the octβ2r mutant genetic background for rescue experiments.

Fecundity Tests.

For ovulation analysis, virgin females were collected within 12 h after eclosion and aged for 4 to 5 days before tests. Ten virgin females were placed with thirty CS males in a food vial for 18 h for mating and then were anaesthetized on ice. The female reproductive system was dissected to determine the presence of an egg in the lateral or common oviduct, or uterus. The percentage of females with an egg per vial was used as one data point. In the experiments involving HS-GAL4, the control and transgenic octβ2r mutant females reared at room temperature were treated with heat shock at 37° C. for 30 min twice with a 5 h interval. After 4 h of recovery at room temperature, they were subjected to mating and ovulation tests. For progeny counts, three virgin females and six CS males were placed in a food vial for three days and then removed. The number of progeny was counted 14 days later. In sperm retention analysis, CS or octβ2r virgin females were mated with dj-GFP males, in which sperm is tagged with GFP. The female reproductive system was dissected 24 or 48 h later and processed as described in the Histological analysis section below.

Behavioral Tests.

For courtship, copulation, and receptivity analyses, 4 day-old CS or octβ2r virgin females were individually paired with CS males in a courtship chamber and videotaped to score courtship activity, copulation initiation time and copulation duration (Lee et al. *Dev. Biol.* 2003, 264:179-190; Zhou et al. *The Journal of neuroscience: the official journal of the Society for Neuroscience.* 2012, 32:14281-14287). The percentage of time that a male spent courting a female during the first 10 min of pairing was used as courtship index (CI). In receptivity tests, the females mated with CS males were gently transferred to a food vial and housed alone. After 48 h they were individually paired with naïve CS males and videotaped to measure courtship and copulation activities.

Histological Analysis.

The female reproductive system that includes the ovary, oviduct, uterus, sperm storage organs, and accessory glands was dissected in phosphate buffered saline (PBS) and fixed in PBS containing 4% paraformaldehyde for 20 min at room temperature (Lee et al. *PLoS One.* 2009, 4:e4716). For cryosections, whole female flies were fixed in PBS containing 4% paraformaldehyde and 40 mM lysine for 3 h and soaked in 25% sucrose solution overnight at 4° C. Ten micron sagittal sections were made and placed on a Superfrost microscope slide (Thermo Fisher Scientific, Waltham, Mass.). The dissected and cryosectioned tissues were then washed with PBS and 0.12 M Tris-HCl, pH 7.4, three times for 10 min each and mounted in the Vectashield mounting medium containing DAPI (Vector Labs, Burlingame, Calif.). Images were collected using the Zeiss LSM 700 confocal microscope (Carl Zeiss, Thornwood, N.Y.) and processed using the Image J software (NIH).

RNA Analysis.

The female reproductive system was dissected as mentioned above and ovaries were taken out to enrich RNA from the oviduct. Fifty dissected tissues were pooled and homogenized in lysis buffer RLT (Qiagen, Valencia, Calif.) with the Kontes micro tissue grinder (Thermo Fisher Scientific) followed by the QIAshredder spin column (Qiagen). Total RNA was extracted using RNeasy Protect Mini kit (Qiagen) and cDNA was synthesized using SuperScript III First-Strand Synthesis System (Invitrogen, Carlsbad, Calif.) for PCR. Quantitative PCR (qPCR) was performed and analyzed using the iQ SYBR Green Supermix kit (Bio-Rad, Hercules, Calif.) in the MyIQ Single-Color Real-Time PCR detection system (Bio-Rad) according to the manufacturer's instructions. Twenty to 100 ng of cDNA samples were run in triplicates and the reactions were done with two different primer sets for individual receptors and ribosomal protein L32 (Rp49; Gabler et al. *Genetics.* 2005, 169:723-736; Daborn et al. *Science.* 2002, 297:2253-2256), which was used as a reference gene to normalize receptor expression levels. All primer sets were designed to span at least one intron and checked for specificity using the Flybase Blast against the *Drosophila* genome (Flybase-Consortium. *Nucleic Acids Res.* 2003, 31:172-175). The PCR primers were: for Octβ1R, F1-TGTGCAGCCACTGGACTATC (SEQ ID NO:1), R1-TATGGCGTATGCCTTGTTCA (SEQ ID NO:2), F2-AGCATCATGCACCTCTGTTG (SEQ ID NO:3), R2-GTGTACCATCCCGAGCAGAT (SEQ ID NO:4); for Octβ3R, F1-ATTTCAGTGCAGCGCAATC (SEQ ID NO:5), R1-CATCCAGGCTGTTGTACACG (SEQ ID NO:6), F2-TTCCACGTTTGAGCTCCTCT (SEQ ID NO:7), R2-GCCAGCGACACAACAAAGTA (SEQ ID NO:8); for Rp49, F1-TACAGGCCCAAGATCGTGAA (SEQ ID NO:9), R1-GTTCGATCCGTAACCGATGT (SEQ ID NO:10), F2-CGCACCAAGCACTTCATCC (SEQ ID NO:11), R2-AGCGGCGACGCACTCTGT (SEQ ID NO:12).

Data Analysis.

Statistical analyses were performed using Minitab 16 (Minitab, State College, Pa.) and JMP 10 (SAS, Cary, N.C.). All data are presented as mean SEM and normality was determined by the Anderson Darling goodness-of-fit test. Normally distributed data were analyzed with Student's t-test or ANOVA and post hoc Tukey-Kramer tests while non-normally distributed data typically observed in courtship indices or fecundity data with many values close to zero were analyzed by Kruskal-Wallis and post hoc Mann-Whitney tests.

The invention claimed is:

1. A method of reducing fecundity in an insect comprising administering to an insect phentolamine.

2. The method of claim 1, further comprising administering an OAMB antagonists, a PKA inhibitor, a CaMKII inhibitor, or combinations thereof.

3. The method of claim 1, wherein the Octβ2R antagonist is formulated in an insect control composition.

4. The method of claim 3, wherein the insect control composition further comprises an insect toxicant.

5. The method of claim 3, wherein the insect control composition further comprises an additional bioactive compound.

6. The method of claim 1, wherein the insect is medfly, fruit fly, or mosquito.

7. The method of claim 1, wherein the insect is a spotted wing *drosophila*.

* * * * *